(12) United States Patent
Cheung et al.

(10) Patent No.: US 9,273,313 B2
(45) Date of Patent: Mar. 1, 2016

(54) ACTIVATION OF QUIESCENT STEM CELLS

(71) Applicants: The Board of Trustees of the Leland Stanford Junior University, Palo Alto, CA (US); The United States of America as represented by the Department of Veterans Affairs, Washington, DC (US)

(72) Inventors: Hiu Tung Cheung, Palo Alto, CA (US); Thomas A. Rando, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/179,417

(22) Filed: Feb. 12, 2014

(65) Prior Publication Data

US 2014/0249205 A1    Sep. 4, 2014

Related U.S. Application Data

(60) Provisional application No. 61/768,161, filed on Feb. 22, 2013.

(51) Int. Cl.
*C12N 15/11* (2006.01)
*C12N 15/113* (2010.01)

(52) U.S. Cl.
CPC ........ *C12N 15/113* (2013.01); *C12N 2310/113* (2013.01); *C12N 2310/315* (2013.01); *C12N 2310/341* (2013.01); *C12N 2310/3515* (2013.01)

(58) Field of Classification Search
CPC ........... C12N 15/113; C12N 2310/113; C12N 2310/315; C12N 2310/341
See application file for complete search history.

(56) References Cited

U.S. PATENT DOCUMENTS

| 8,580,757 | B2 * | 11/2013 | Federov et al. | 514/44 A |
| 2011/0218141 | A1 * | 9/2011 | Hamrick | 514/4.9 |

FOREIGN PATENT DOCUMENTS

| WO | WO 2009/023523 | | 2/2009 |
| WO | WO 2009/023525 | A2 * | 2/2009 |

OTHER PUBLICATIONS

Eisenberg et al. PNAS 2007, pp. 399, 17016-17021 and table 4 and corrections.*
Cerletti et al., "Response: Skeletal Muscle Precursor Grafts in Dystrophic Mice", Cell, 2008, 998-999.
Cheung et al., "Maintenance of Muscle Stem-Cell Quiescence by microRNA-489", Nature, 2012, 482(7386):524-528.
Collins et al., "Stem Cell Function, Self-Renewal, and Behavioral Heterogeneity of Cells from the Adult Muscle Satellite Cell Niche", Cell, 2005, 122:289-301.
Cornelison et al., "Syndecan-3 and Syndecan-4 Specifically Mark Skeletal Muscle Satellite Cells and are Implicated in Satellite Cell Maintenance and Muscle Regeneration", Dev. Biol., 2001, 239(1):79-94.
Fukada et al., "Purification and Cell-Surface Marker Characterization of Quiescent Satellite Cells from Murine Skeletal Muscle by a Novel Monoclonal Antibody", Exp. Cell Res., 2004, 296(2):245-255.
Galvez et al., "Complete Repair of Dystrophic Skeletal Muscle by Mesoangioblasts with Enhanced Migration Ability", J. Cell Biol., 2006, 174(2):231-243.
Kikkawa et al., "miR-489 is a Tumour-Suppressive miRNA Target PTPN11 in Hypopharyngeal Squamous Cell Carcinoma (HSCC)", Br. J. Cancer, 2010, 103(6):877-884.
Kuang et al., "Asymmetric Self-Renewal and Commitment of Satellite Stem Cells in Muscle", Cell, 2007, 129(5):999-1010.
Montarras et al., "Direct Isolation of Satellite Cells for Skeletal Muscle Regeneration", Science, 2005, 309(5743):2064-2067.
Sacco et al., "Self-Renewal and Expansion of Single Transplanted Muscle Stem Cells", Nature, 2008, 456(7221):502-506.
Sampaolesi et al., "Cell Therapy of α-Sarcoglycan Null Dystrophic Mice Through Intra-Arterial Delivery of Mesoangioblasts", Science, 2003, 301(5632):487-492.
Schoolmeesters et al., "Functional Profiling Reveals Critical Role for miRNA in Differentiation of Human Mesenchymal Stem Cells", PLoS One, 2009, 4(5):e5605.
Sherwood et al., "Isolation of Adult Mouse Myogenic Progenitors: Functional Heterogeneity of Cells within and Engrafting Skeletal Muscle", Cell, 2004, 119:543-554.

* cited by examiner

*Primary Examiner* — Brian Whiteman
(74) *Attorney, Agent, or Firm* — Pamela J. Sherwood; Bozicevic, Field & Francis LLP

(57) ABSTRACT

Compositions and methods are provided for altering the activation of quiescent stem cells by modulating activity of the microRNA miR-489.

10 Claims, 19 Drawing Sheets
(16 of 19 Drawing Sheet(s) Filed in Color)

a b

ACTIVATION OF QUIESCENT STEM CELLS

GOVERNMENT SUPPORT

This invention was made with Government support under contracts OD000392 and AG036695 awarded by the National Institutes of Health. The Government has certain rights in the invention.

BACKGROUND OF THE INVENTION

Among the key properties that distinguish adult mammalian stem cells from their more differentiated progeny is the ability of stem cells to remain in a quiescent state for prolonged periods of time (Li & Clevers, Science 327, 542-545 (2010)), (Fuchs, Cell 137, 811-819 (2009)). Quiescence is a common feature of stem cells characterized by reversible mitotic arrest and reduced metabolic activity that protects stem cells against endogenous stress caused by DNA replication and cellular respiration. Quiescence of stem cells is critical to ensure lifelong tissue maintenance and to protect the stem cell pool from premature exhaustion under conditions of various stresses. However, the molecular pathways for the maintenance of stem-cell quiescence remain elusive.

Stem cells have a capacity both for self-renewal and the generation of differentiated cell types, which provides the possibility for therapeutic regeneration of cells and tissues in the body. In addition to studying the important normal function of stem cells in the regeneration of tissues, researchers have further sought to exploit the potential of in situ and/or exogenous stem cells for the treatment of a variety of disorders. While early, embryonic stem cells have generated considerable interest, the stem cells resident in adult tissues also provide an important source of regenerative capacity.

These somatic, or adult, stem cells are undifferentiated cells that reside in differentiated tissues, and have the properties of both self-renewal and generation of differentiated cell types. The differentiated cell types may include all or some of the specialized cells in the tissue. For example, hematopoietic stem cells give rise to all hematopoietic lineages, but do not seem to give rise to stromal and other cells found in the bone marrow. Sources of somatic stem cells include bone marrow, blood, the cornea and the retina of the eye, brain, skeletal muscle, cartilage, bones, dental pulp, liver, skin, the lining of the gastrointestinal tract, and pancreas, and the like. Adult stem cells are usually quite sparse. Often they are difficult to identify, isolate, and purify. Often, somatic stem cells are quiescent until stimulated by the appropriate growth signals.

Muscle tissue in adult vertebrates regenerates from stem cells known as satellite cells. Satellite cells are distributed throughout muscle tissue and are mitotically quiescent in the absence of injury or disease, residing in an instructive, anatomically defined niche. The satellite cell niche constitutes a distinct membrane-enclosed compartment within the muscle fiber, containing a diversity of biochemical and biophysical signals that influence satellite cell function. In addition to satellite cells, cell types that contribute to muscle regeneration include mesangioblasts, bone marrow derived cells, muscle interstitial cells, mesenchymal stem cells, etc. See D. D. Cornelison et al. (2001) Dev Biol 239, 79; S. Fukada et al. (2004) Exp Cell Res 296, 245; D. Montarras et al. (2005) Science 309, 2064; S. Kuang et al. (2007) Cell 129, 999; M. Cerletti et al. (2008) Cell 134, 37; C. A. Collins et al. (2005) Cell 122, 289; A. Sacco et al. (2008) Nature 456, 502; R. I. Sherwood et al. (2004) Cell 119, 543; Sampaolesi et al. (2003) Science 301(5632):487-92; and Galvez et al. (2006) J Cell Biol. 174(2):231-43.

Satellite cells are the primary cells in muscle tissue required for the regeneration that occurs in response to injury or disease. In response to injury, SCs are activated and they proliferate and differentiate into myoblasts that undergo further differentiation and fusion to form muscle fibers. Methods of manipulating activation are of great interest for therapeutic applications.

SUMMARY OF THE INVENTION

Methods are provided for the modulation of stem cell activation, including the activation of quiescent stem cells, for example muscle stem cells. It is shown herein that the microRNA (miRNA) pathway is essential for the maintenance of the quiescent state. Specifically, miRNA-489 (miR-489) is highly expressed in quiescent stem cells and is quickly downregulated during stem-cell activation. miR-489 functions as a regulator of satellite-cell quiescence by suppressing Dek, which protein localizes to the more differentiated daughter cell during asymmetric division of satellite cells and promotes the transient proliferative expansion of myogenic progenitors.

In some embodiments of the invention, a quiescent stem cell is contacted with an inhibitor of miR-489, wherein the stem cell is activated and proliferates. The contacting may be performed in vitro or in vivo, e.g. by localized or system administration of the inhibitor. The inhibition of microRNA-489 may presents a therapeutic application in enhancing muscle regeneration.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE SPECIFIC EMBODIMENTS

Figure 1:
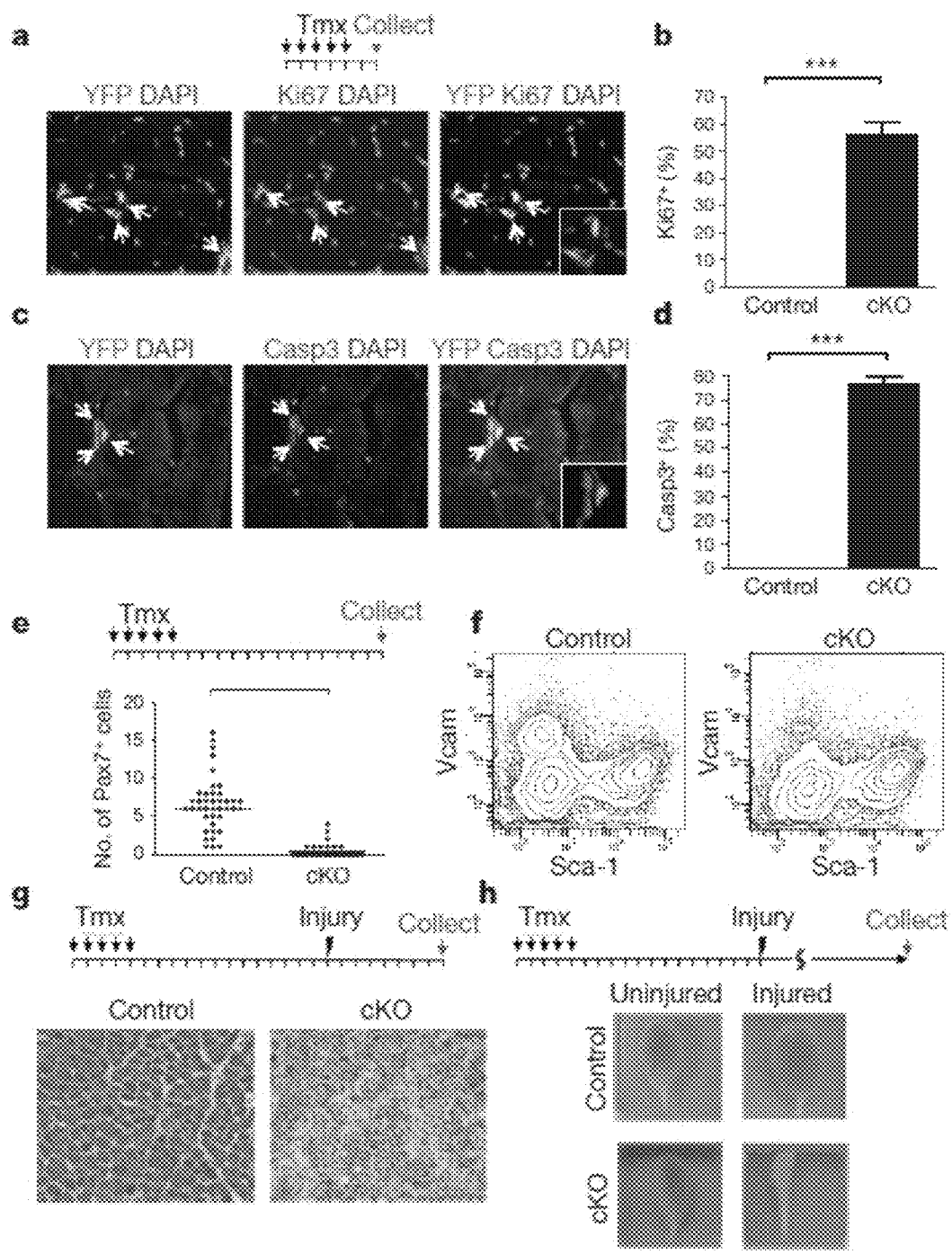
FIG. 1 The miRNA pathway is essential for the maintenance of satellite-cell quiescence and survival of activated satellite cells. A, The tamoxifen (Tmx) injection scheme (black arrows) for conditional Dicer gene inactivation is shown (top). Each tick represents 1 day. Six days after the first injection, Ki67 YFP double-positive satellite cells were found (white arrows). Nuclei were stained with DAPI. B, Quantification of the percentage of YFP-positive cells that were Ki67-positive (Ki67+) in control and conditional knockout strain (cKO) mice (*$P<0.001$). C, Six days after the first tamoxifen injection, muscles from control or cKO mice were analysed for apoptosis by staining for cleaved caspase 3. Nuclei were stained with DAPI. Inset in A and C, magnified view of the satellite cells in the full-size images. D, Quantification of the percentage of YFP-positive cells that were caspase-3-positive (Casp3+) in control and cKO animals (*$P<0.001$). E, Satellite-cell numbers were quantified on freshly isolated single fibres from control and cKO mice 2 weeks after tamoxifen injections (*$P<0.001$). F, Satellite-cell numbers were quantified by FACS analyses of mononuclear cells from hindlimb muscles of control and cKO mice. Satellite cells are shown in orange in these representative FACS plots (See FIG. 8). In four replicates, the percentage of satellite cells in total mononuclear cells in cKO muscles was markedly reduced (0.7%) compared to that in control muscles (3.0%). Blue, all other mononuclear cells. G, Tibialis anterior muscles from control or cKO mice were injured 2 weeks after tamoxifen injection and cryosections were stained with haematoxylin and eosin 7 days after injury. H, Tibialis anterior muscles from control or cKO mice were injured 2 weeks after tamoxifen injection and collected 6 months after injury. Severe muscle loss was observed in injured muscles from cKO mice only (shown next to the contralateral, uninjured muscle for comparison). Error bars in B and D indicate s.e.m.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Compositions

MicroRNAs (miRNAs) are an abundant class of non-coding RNAs that are believed to be important in many biological processes through regulation of gene expression. These non-coding RNAs that can play important roles in development by targeting the messages of protein-coding genes for cleavage or repression of productive translation. Humans have between 200 and 255 genes that encode miRNAs, an abundance corresponding to almost 1% of the protein-coding genes.

MicroRNAs of interest for use in the methods of the invention include those natural RNAs expressed in quiescent stem cells, in particular miR-489. The nucleotide sequence of representative miR-489 sequences is provided in Table 1. It can be seen that the sequence is very highly conserved among primate and mammalian species.

TABLE 1 miR-489 Sequences

| organism | Mirbank accession | Stem Loop sequence | Mature sequence |
|---|---|---|---|
| Homo sapiens | MI0003124 | GUGGCAGCUUGGUGGUCGUAUGUGUGACGCCAUUUACUU GAACCUUUAGGAGUGACAUCACAUAUACGGCAGCUAAACU GCUAC (SEQ ID NO. 5) | GUGACAUCACAUAU ACGGCAGC (SEQ ID NO. 13) |
| Macaca mulatta | MI0007763 | GUGGCAGCUUGGUGGUCGUAUGUGUGGCGCCAUUUACUU GAACCUUUAGGAGUGACAUCACAUAUACGGCAGCUAAACU GUUAC (SEQ ID NO. 6) | GUGACAUCACAUAU ACGGCAGC (SEQ ID NO. 13) |
| Pongo pygmaeus | MI0014962 | GUGGCAGCUUGGUGGUCGUAUGUGUGGCGCCAUUUACUU GAACCUUUAGGAGUGACAUCACAUAUACGGCAGCUAAACU GCUAC (SEQ ID NO. 7) | GUGACAUCACAUAU ACGGCAGC (SEQ ID NO. 13) |
| Pan troglodytes | MI0008686 | GUGGCAGCUUGGUGGUCGUAUGUGUGACGCCAUUUACUU GAACCUUUAGGAGUGACAUCACAUAUACGGCAGCUAAACU GCUA (SEQ ID NO. 8) | GUGACAUCACAUAU ACGGCAGC (SEQ ID NO. 13) |
| Bos Taurus | MI0010441 | GUGGCAGCUUGGUGGUCGUAUGUGUGGCGCCAUCUACUG GAACGUUUAGGAGUGACAUCACAUAUAUGGCGACUAAACU GCU (SEQ ID NO. 9) | |
| Canis familiaris | MI0010355 | GUGGCAGCUUGGUGGCCGUAUGUGUGGCGCCAUUUACUU GAACCUUUAGGAGUGACAUCACAUAUACGGCGGCUAAACU GCUAC (SEQ ID NO. 10) | GUGACAUCACAUAU ACGGCGGC (SEQ ID NO. 14) |
| Mus musculus | MI0003476 | ACUGCUGCAGUGGCAGCUUGGUUGUCAUAUGUGUGAUGA CACUUUCUAAAGUCUUCCAGAAUGACACCACAUAUAUGGC AGCUAAACUGUUACAUGGAACAACAAGU (SEQ ID NO. 11) | AAUGACACCACAUA UAUGGCAGC (SEQ ID NO. 15) |
| Rattus norvegicus | MI0003477 | ACUGCUACAGUGGCAGCUUGGUUGUCGUAUGCGUGAUGA CACGUUCUCGUGUAUUCCAGAAUGACAUCACAUAUAUGGC AGCUAAACUGUUACAGGAACAACAAGU (SEQ ID NO. 12) | UGUCGUAUGCGUG AUGACACGUUC (SEQ ID NO. 16) |

As used herein, the term miR-489 may refer to any of the provided sequences, usually in reference to a polynucleotide comprising the sequence GUGACAUCACAUAUACG-GCAGC (SEQ ID NO:13). Included in the scope of the term "microRNA" is included synthetic molecules with substantially the same activity as the native microRNA, e.g. synthetic oligonucleotides having altered chemistries, as are known in the art.

In practicing the subject methods, an effective amount of a miR489 agent, for example a miR489 inhibitor, is introduced into the target cell, where any convenient protocol for introducing the agent into the target cell may be employed. The target cell is usually a stem cell, including, without limitation, hematopoietic stem cells, muscle satellite cells, and the like.

The subject methods are used for prophylactic or therapeutic purposes. As used herein, the term "treating" is used to refer to both prevention of disease, and treatment of pre-existing conditions. For example, the prevention of autoimmune disease may be accomplished by administration of the agent prior to development of overt disease. The treatment of ongoing disease, where the treatment stabilizes or improves the clinical symptoms of the patient, is of particular interest.

As is known in the art, miRNAs are single stranded RNA molecules that range in length from about 20 to about 25 nt, such as from about 21 to about 24 nt, e.g., 22 or 23 nt. The target miR-489 may or may not be completely complementary to the introduced miR-489 agent. If not completely complementary, the miRNA and its corresponding target viral genome are at least substantially complementary, such that the amount of mismatches present over the length of the miRNA, (ranging from about 20 to about 25 nt) will not exceed about 8 nt, and will in certain embodiments not exceed about 6 or 5 nt, e.g., 4 nt, 3 nt, 2 nt or 1 nt.

The miR-489 agent may increase or decrease the levels of miR-489 in the targeted cell. Where the agent is an inhibitory agent, it inhibits the activity of the target miRNA by reducing the amount of miR-489 RNA present in the targeted cells, where the target cell may be present in vitro or in vivo. By "reducing the amount of" is meant that the level or quantity of the target miRNA in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods.

Where the miR-489 agent increases the activity of the targeted miRNA in a cell, the amount of miR-489 is increased in the targeted cells, where the target cell may be present in vitro or in vivo. By "increasing the amount of" is meant that the level or quantity of the target miRNA in the target cell is increased by at least about 2-fold, usually by at least about 5-fold, e.g., 10-fold, 15-fold, 20-fold, 50-fold, 100-fold or more, as compared to a control, i.e., an identical target cell not treated according to the subject methods.

By miRNA inhibitory agent is meant an agent that inhibits the activity of the target miRNA. Such an agent finds use where ectivation of a stem cell is of interest, i.e. to break quiescence of the stem cell. The inhibitory agent may inhibit the activity of the target miRNA by a variety of different mechanisms. In certain embodiments, the inhibitory agent is one that binds to the target miRNA and, in doing so, inhibits its activity. Representative miRNA inhibitory agents include, but are not limited to: antisense oligonucleotides, and the like. Other agents of interest include, but are not limited to: Naturally occurring or synthetic small molecule compounds of interest, which include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing appropriate screening protocols.

The antisense reagent may be antisense oligonucleotides (ODN), particularly synthetic ODN having chemical modifications from native nucleic acids, or nucleic acid constructs that express such antisense molecules as RNA. The antisense sequence is complementary to the targeted miRNA, and inhibits its expression. One or a combination of antisense molecules may be administered, where a combination may comprise multiple different sequences.

Antisense molecules may be produced by expression of all or a part of the target miRNA sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 25, usually not more than about 21-22 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha.-anomer of deoxyribose may be used, where the base is inverted with respect to the natural .beta.-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Anti-sense molecules of interest include antagomir RNAs, e.g. as described by Krutzfeldt et al., supra., herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing miRNAs in vivo, chemically modified, cholesterol-conjugated single-stranded RNA analogues complementary to miRNAs were developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

Also of interest in certain embodiments are RNAi agents. In representative embodiments, the RNAi agent targets the precursor molecule of the microRNA, known as pre-microRNA molecule. By RNAi agent is meant an agent that modulates expression of microRNA by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

Alternatively, where it is desirable to increase miR-489 expression in a cell, e.g. to maintain stem cell quiescence, an agent may be miR-489 microRNA itself or a vector that that expresses miR-489, including the pre-miRNA sequence relevant to the targeted organism, which agent can include any of the modified oligonucleotides described above with respect to antisense, e.g. cholesterol conjugates, phosphorothioates linkages, and the like. Alternatively, a vector.

Expression vectors may be used to introduce the target gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The expression cassette will generally employ an exogenous transcriptional initiation region, i.e. a promoter other than the promoter which is associated with the T cell receptor in the normally occurring chromosome. The promoter is functional in host cells, particularly host cells targeted by the cassette. The promoter may be introduced by recombinant methods in vitro, or as the result of homologous integration of the sequence by a suitable host cell. The promoter is operably linked to the coding sequence of the autoantigen to produce a translatable mRNA transcript. Expression vectors conveniently will have restriction sites located near the promoter sequence to facilitate the insertion of autoantigen sequences.

Expression cassettes are prepared comprising a transcription initiation region, which may be constitutive or inducible, the gene encoding the autoantigen sequence, and a transcriptional termination region. The expression cassettes may be introduced into a variety of vectors. Promoters of interest may be inducible or constitutive, usually constitutive, and will provide for high levels of transcription in the vaccine recipient cells. The promoter may be active only in the recipient cell type, or may be broadly active in many different cell types. Many strong promoters for mammalian cells are known in the art, including the .beta.-actin promoter, SV40 early and late promoters, immunoglobulin promoter, human cytomegalovirus promoter, retroviral LTRs, etc. The promoters may or may not be associated with enhancers, where the enhancers may be naturally associated with the particular promoter or associated with a different promoter.

A termination region is provided 3' to the coding region, where the termination region may be naturally associated with the variable region domain or may be derived from a different source. A wide variety of termination regions may be employed without adversely affecting expression.

The various manipulations may be carried out in vitro or may be performed in an appropriate host, e.g. *E. coli*. After each manipulation, the resulting construct may be cloned, the vector isolated, and the DNA screened or sequenced to ensure the correctness of the construct. The sequence may be screened by restriction analysis, sequencing, or the like.

Cells

Stem Cell:

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or asymmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Somatic Stem Cells:

Somatic stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells (including without limitation satellite cells as described herein); hematopoietic stem cells, epithelial stem cells, neural stem cells; mesenchymal stem cells; and the like.

Stem cells of particular interest are muscle stem cells, which may be evidenced by the ability to engraft and repopulate the myofiber-associated compartment in vivo following intramuscular injection, and subsequent maintenance of myogenic-colony forming capacity. Muscle cells include skeletal, cardiac and smooth muscles, but particularly skeletal muscle.

The stem cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

The term "muscle cell" as used herein refers to any cell which contributes to muscle tissue. Myoblasts, satellite cells, myotubes, and myofibril tissues are all included in the term "muscle cells". Muscle cell effects may be induced within skeletal, cardiac and smooth muscles. Muscle tissue in adult vertebrates regenerates from reserve myoblasts called "satellite cells". or mesangioblasts, bone marrow derived cells, muscle interstitial cells, mesenchymal stem cells, etc. Satellite cells are distributed throughout muscle tissue and are mitotically quiescent in the absence of injury or disease. Following muscle injury or during recovery from disease, satellite cells reenter the cell cycle, proliferate and 1) enter existing muscle fibers or 2) undergo differentiation into multinucleate myotubes which form new muscle fiber. The myoblasts ultimately yield replacement muscle fibers or fuse into existing muscle fibers, thereby increasing fiber girth by the synthesis of contractile apparatus components. This process is illustrated, for example, by the nearly complete regeneration which occurs in mammals following induced muscle fiber degeneration; the muscle progenitor cells proliferate and fuse together regenerating muscle fibers.

One example of muscle stem cells is cells characterized as CD45⁻, CD11b⁻, CD31⁻, Sca1⁻, α7 integrin⁺, and CD34'. Various other criteria have been used to select for muscle stem cells, including without limitation: enrichment for (CD11b/CD31/Sca1/CD45)– CD34+ alpha7integrin+(see Sacco et al. (2008) Nature 456(7221):502-506); enrichment for (Sca1/Mac1/CD45)-CD29+CXCR4+(see Cerletti et al. (2008) Cell 134(1):37-47); enrichment for Syndecan3+/Syndecan4+/ABCG2-/Sca– (see Tanaka et al. (2009) Cell Stem Cell. 4(3):217-25); use of whole single muscle fibers (see Collins et al. (2005) Cell 122(2):289-301); enrichment for lineage-negative alpha7integrin+ betalintegrin+ cells (see Kuang et al. (2007) Cell 129(5):999-1010); enrichment with SMC2.6 antibody (see Fukada et al. (2004) Exp Cell Res. 296(2):245-55); enrichment from pericytes of CD56+(NCAM) (see Meng et al. (2011) PLoS One. 6(3):e17454); and enrichment for CD34– CD56+ cells (see Pisani et al. (2010) Stem Cells 28(4):753-64); each reference herein specifically incorporated by reference.

Muscle regeneration as used herein refers to the process by which new muscle fibers form from muscle progenitor cells. A therapeutic composition will usually confer an increase in the number of new fibers by at least 1%, more preferably by at least 20%, and most preferably by at least 50%. The growth of muscle may occur by the increase in the fiber size and/or by increasing the number of fibers. The growth of muscle may be measured by an increase in wet weight, an increase in protein content, an increase in the number of muscle fibers, an increase in muscle fiber diameter; etc. An increase in growth of a muscle fiber can be defined as an increase in the diameter where the diameter is defined as the minor axis of ellipsis of the cross section.

Muscle regeneration can also be monitored by the mitotic index of muscle. For example, cells may be exposed to a labeling agent for a time equivalent to two doubling times. The mitotic index is the fraction of cells in the culture which have labeled nuclei when grown in the presence of a tracer which only incorporates during S phase (i.e., BrdU) and the doubling time is defined as the average S time required for the number of cells in the culture to increase by a factor of two. Alternatively, activation in vivo may be detected by monitoring the appearance of the intermediate filament vimentin by immunological or RNA analysis methods. When vimentin is assayed, a useful activator may cause expression of detectable levels of vimentin in the muscle tissue when the therapeutically useful dosage is provided. Productive muscle regeneration may be also monitored by an increase in muscle strength and agility.

Muscle regeneration may also be measured by quantitation of myogenesis, i.e. fusion of myoblasts to yield myotubes. An effect on myogenesis results in an increase in the fusion of myoblasts and the enablement of the muscle differentiation program. For example, the myogenesis may be measured by the fraction of nuclei present in multinucleated cells in relative to the total number of nuclei present. Myogenesis may also be determined by assaying the number of nuclei per area in myotubes or by measurement of the levels of muscle specific protein by Western analysis.

The survival of muscle fibers may refer to the prevention of loss of muscle fibers as evidenced by necrosis or apoptosis or the prevention of other mechanisms of muscle fiber loss. Muscles can be lost from injury, atrophy, and the like, where atrophy of muscle refers to a significant loss in muscle fiber girth.

Methods

For the treatment of disorders in which there is inadequate stem cell activation or there is a rapid deterioration of tissues due to an injury or disease, a miR489 inhibitor is administered at a dose that is effective to cause an increase of stem cell activation, but which maintains the overall health of the individual. Activation of muscle stem cells is of particular interest. Treatment regimens may utilize a short-term administration of the active agent; although the treatment may be repeated as necessary. The treatment regime can require administration for prolonged periods, but may be administered as a single dose monthly, semi-monthly, etc. The size of the dose administered must be determined by a physician and will depend on a number of factors, such as the nature and gravity of the disease, the age and state of health of the patient and the patient's tolerance to the drug itself.

In a specific embodiment, the miR489 inhibitor is used for treatment of patients requiring activation of muscle stem cells by means of a short-term administration, e.g. of 1, 2, 3 or more days, up to 1 or 2 weeks, in order to obtain a rapid, significant increase in activation, e.g. with daily or semi-daily administration.

Diseases of interest for treatment with the methods of the invention include heritable and acquired muscle disorders, e.g. of skeletal muscle. A number of muscle conditions in which there is muscle wasting such as cachexia, atrophy and sarcopenia, are of interest, e.g. conditions associated with increased age, immobility, drug treatment, cancer, and the like. In addition to skeletal muscle formation, the regeneration of cardiac muscle in the aging is of interest. For example, following an event such as myocardial infarction; surgery, catheter insertion, atherosclerosis, and the like, cardiac muscle can be damaged. Such damage is not easily repaired in elderly patients, resulting in a loss of function. Administration of miR-489 inhibitors following such incidents of muscle damage can increase regeneration of the damaged tissues. The agents may be administered systemically, or using a stent, catheter, implant, and the like that increase the local concentration of the active agent.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention.

Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests.

In some embodiments, the inherited muscle disorders include, without limitation, muscular dystrophies. For example, Duchenne dystrophy is an X-linked recessive disorder characterized by progressive proximal muscle weakness with destruction and regeneration of muscle fibers and replacement by connective tissue. Duchenne dystrophy is caused by a mutation at the Xp21 locus, which results in the absence of dystrophin, a protein found inside the muscle cell membrane. It affects 1 in 3000 live male births. Symptoms typically start in boys aged 3 to 7 yr.

Progression is steady, and limb flexion contractures and scoliosis develop. Firm pseudohypertrophy (fatty and fibrous replacement of certain enlarged muscle groups, notably the calves) develops. Becker muscular dystrophy is a less severe variant, also due to a mutation at the Xp21 locus. Dystrophin is reduced in quantity or in molecular weight. Patients usually remain ambulatory, and most survive into their 30s and 40s.

In some embodiments, muscle disorders include myopathies. In some embodiments, myopathies include, but are not limited to, congenital and metabolic myopathies, including glycogen storage diseases and mitochondrial myopathies. Congenital myopathies are a heterogeneous group of disorders that cause hypotonia in infancy or weakness and delayed motor milestones later in childhood. An autosomal dominant form of nemaline myopathy is linked to chromosome 1 (tropomyosin gene), and a recessive form to chromosome 2. Other forms are caused by mutations in the gene for the ryanodine receptor (the calcium release channel of the sarcoplasmic reticulum) on chromosome 19q. Skeletal abnormalities and dysmorphic features are common. Diagnosis is made by histochemical and electron microscopic examination of a muscle sample to identify specific morphologic changes.

Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendelian inheritance pattern. Mutations in nuclear-encoded mitochondrial enzymes occur.

Glycogen storage diseases of muscle are a group of rare autosomal recessive diseases characterized by abnormal accumulation of glycogen in skeletal muscle due to a specific biochemical defect in carbohydrate metabolism. These diseases can be mild or severe. In a severe form, acid maltase deficiency (Pompe's disease), in which 1,4-glucosidase is absent, is evident in the first year of life and is fatal by age 2. Glycogen accumulates in the heart, liver, muscles, and nerves. In a less severe form, this deficiency may produce proximal limb weakness and diaphragm involvement causing hypoventilation in adults. Myotonic discharges in paraspinal muscles are commonly seen on electromyogram, but myotonia does not occur clinically. Other enzyme deficiencies cause painful cramps after exercise, followed by myoglobinuria. The diagnosis is supported by an ischemic exercise test without an appropriate rise in serum lactate and is confirmed by demonstrating a specific enzyme abnormality.

Channelopathies are neuromuscular disorders with functional abnormalities due to disturbance of the membrane conduction system, resulting from mutations affecting ion channels. Myotonic disorders are characterized by abnormally slow relaxation after voluntary muscle contraction due to a muscle membrane abnormality.

Myotonic dystrophy (Steinert's disease) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities. Mental retardation is common. Severely affected persons die by their early 50s.

Myotonia congenita (Thomsen's disease) is a rare autosomal dominant myotonia that usually begins in infancy. In several families, the disorder has been linked to a region on chromosome 7 containing a skeletal muscle chloride channel gene. Painless muscle stiffness is most troublesome in the hands, legs, and eyelids and improves with exercise. Weakness is usually minimal. Muscles may become hypertrophied. Diagnosis is usually established by the characteristic physical appearance, by inability to release the handgrip rapidly, and by sustained muscle contraction after direct muscle percussion.

Familial periodic paralysis is a group of rare autosomal dominant disorders characterized by episodes of flaccid paralysis with loss of deep tendon reflexes and failure of muscle to respond to electrical stimulation. The hypokalemic form is due to genetic mutation in the dihydropyridine receptor-associated calcium channel gene on chromosome 1q. The hyperkalemic form is due to mutations in the gene on chromosome 17q that encodes a subunit of the skeletal muscle sodium channel (SCN4A).

Sarcopenia is a term utilized to define the loss of muscle mass and strength that occurs with aging. Sarcopenia is believed to play a major role in the pathogenesis of frailty and functional impairment that occurs with old age. Progressive muscle wasting occurs with aging. The prevalence of clinically significant sarcopenia is estimated to range from 8.8% in young old women to 17.5% in old old men. Persons who are obese and sarcopenic (the "fat frail") have worse outcomes than those who are sarcopenic and non-obese. There is a disproportionate atrophy of type IIa muscle fibers with aging. There is also evidence of an age-related decrease in the synthesis rate of myosin heavy chain proteins. Motor units innervating muscle decline with aging, and there is increased irregularity of muscle unit firing. There are indications that cytokines, especially interleukin-1beta, tumor necrosis factor-alpha, and interleukin-6, play a role in the pathogenesis of sarcopenia. Similarly, the decline in anabolic hormones, i.e. testosterone, dehydroepiandrosterone growth hormone, and insulin-like growth factor-I, is also implicated in the sarcopenic process.

Sarcopenia is typically marked by a decrease in the circumference of distinct types of muscle fibers. During sarcopenia, there is a decrease in "type 2" fiber circumference (Type II), with little to no decrease in "type I" fiber circumference (Type I). Diagnosis of sarcopenia may include low muscle mass, >2 standard deviations below that mean measured in young adults (aged 18-39 years in the 3rd NHANES population) of the same sex and ethnic background, and low gait speed (e.g. a walking speed below 0.8 m/s in the 4-m walking test).

Cachexia is wasting of both adipose and skeletal muscle. It occurs in many conditions and is common with many cancers when remission or control fails. Some cancers, especially pancreatic and gastric cancers, cause profound cachexia. Affected patients may lose 10 to 20% of body weight. Men tend to experience worse cachexia with cancer than do women. Neither tumor size nor the extent of metastatic disease predicts the degree of cachexia. Cachexia is associated with reduced response to chemotherapy, poor functional performance, and increased mortality.

The primary cause of cachexia is not anorexia or decreased caloric intake. Rather, this complex metabolic condition involves increased tissue catabolism. Protein synthesis is decreased and degradation increased. Cachexia is mediated by certain cytokines, especially tumor necrosis factor-α, IL-1b, and IL-6, which are produced by tumor cells and host cells in the tissue mass. The ATP-ubiquitin-protease pathway plays a role as well.

Corticosteroid induced myopathy. Steroid muscle-related involvement is a frequent but often underestimated adverse effect of steroid treatment. Clinical presentation may differentiate two features: the less frequent, represented by acute myopathy, essentially observed in resuscitation, in patients treated with high dosages, and the more frequent feature, insidious, painless, chronic myopathy, characterized by a progressive proximal deficit. Diagnosis is mostly based on the clinic, muscle biopsy should remain exceptional, performed to detect other myopathies, since there are no specific anatomopathological findings. Muscle enzymes are rarely increased, electrophysiological analyses demonstrate unspecific and variable abnormalities. Pathophysiology of steroid-induced myopathy is multifactorial, related to protein metabolism modifications (change of both metabolism and catabolism), cellular transcription, growth factors (IGF-1, myostatine).

Unlike with other drug-induced myopathies, serum CK concentration does not markedly increase with steroid myopathy. EMG is normal or may show low amplitude myopathic motor unit potentials and no signs of neuropathy. Muscle biopsy usually reveals an increased variation in the diameter of fibers and type IIb muscle fiber atrophy without muscle fiber inflammation or necrosis. However, a necrotizing steroid myopathy has also been reported to occur. Proximal muscle weakness of the lower and upper extremities is significantly related to the cumulative dose of steroid. An increase in muscle strength occurring 3-4 weeks after dose reduction usually indicates steroid-induced myopathy. However, chronic myopathy may persist after prolonged treatment with high doses of corticosteroids.

In addition to therapeutic uses, the methods of the invention may be used to increase muscle mass and/or decrease body fat in non-human animals, e.g. livestock, including without limitation, equines, bovines, porcines, ursines, etc., for which increased muscle mass may be desired; pets including canines, felines, etc., animal models for research purposes, and the like.

In alternative embodiments, an agent that increases stem cell quiescence is useful in conditions exemplified by hyper-activation of stem cells, e.g. in hyperproliferative conditions such as sarcomas. In such conditions, an agent that icreases miR-489 activity is brought into contact with the activated stem cells in a dose effective to decrease activation of the stem cell.

Depending on the nature of the agent, the active agent(s) may be administered to the host using any convenient means capable of resulting in the desired modulation of miR-489 in the target cell. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means.

Introduction of an effective amount of an miR-489 agent into a mammalian cell as described above results in a modulation of target gene(s) expression, resulting in a modification of the stem cell activation.

The above described methods work in any mammalian cell, where representative mammal cells of interest include, but are not limited to cells of: ungulates or hooved animals, e.g., cattle, goats, pigs, sheep, etc.; rodents, e.g., hamsters, mice, rats, etc.; lagomorphs, e.g., rabbits; primates, e.g., monkeys, baboons, humans, etc.; and the like.

In pharmaceutical dosage forms, the miR-489 agent and/or other compounds may be administered in the form of their pharmaceutically acceptable salts, or they may also be used alone or in appropriate association, as well as in combination with other pharmaceutically active compounds. The agents may be combined to provide a cocktail of activities. The following methods and excipients are exemplary and are not to be construed as limiting the invention.

Those of skill will readily appreciate that dose levels can vary as a function of the specific agent, the severity of the symptoms and the susceptibility of the subject to side effects. Some of the agents will be more potent than others. Preferred dosages for a given agent are readily determinable by those of skill in the art by a variety of means. A preferred means is to measure the physiological potency of a given compound.

As indicated above, the miRNA agent can be introduced into the target cell(s) using any convenient protocol, where the protocol will vary depending on whether the target cells are in vitro or in vivo. A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

For example, the inhibitory agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. For example, the agent may be introduced systemically by parenteral injection, e.g. i.v., i.m. sub-cutaneously, etc. The agent may be appropriately localized in the target site, e.g. muscle tissue, by manipulating the site of injection; by implantation of a reservoir, or depot; which may be a biodregrabable or bioerodible matrix, and the like. Methods for oral introduction include direct mixing of RNA with food of the organism. Physical methods of introducing nucleic acids include injection directly into the cell or extracellular injection into the organism of an RNA solution. The agent may be introduced in an amount which allows delivery of at least one copy per cell. Higher doses (e.g., at least 5, 10, 100, 500 or 1000 copies per cell) of the agent may yield more effective inhibition; lower doses may also be useful for specific applications.

When liposomes are utilized, substrates that bind to a cell-surface membrane protein associated with endocytosis can be attached to the liposome to target the liposome to T cells and to facilitate uptake. Examples of proteins that can be attached include capsid proteins or fragments thereof that bind to T cells, antibodies that specifically bind to cell-surface proteins on T cells that undergo internalization in cycling and proteins that target intracellular localizations within T cells. Gene marking and gene therapy protocols are reviewed by Anderson et al. (1992) Science 256:808-813.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. Patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc.

In alternative embodiments, quiescent stem cells are activated in vitro, e.g. to improve expansion in culture, to enhance the ability to modify stem cells with an exogenous vector, and the like. In such embodiments, a cell, which may be present in culture medium or other acceptable excipient, is contacted with a dose of a miR489 agent effective to modulate activation or quiescence, e.g. an inhibitor in a dose effective to increase cycling of the targeted cell. Such cells can be a defined highly enriched stem cell population, e.g. sorted by column, flow cytometry, etc. for stem cell markers known in the art, or a complex mixture of cells. Muscle stem cells activated by the methods of the invention ex vivo may be implanted into a recipient subject mammal, where the cells or population of cells differentiate into muscle cells.

The term "cell culture" or "culture" means the maintenance of cells in an artificial, in vitro environment. Culture conditions may include, without limitation, a specifically dimensioned container, e.g. flask, roller bottle, plate, 96 well plate, etc.; culture medium comprising suitable factors and nutrients for growth of the desired cell type; and a substrate on the surface of the container or on particles suspended in the culture medium. By "container" is meant a glass, plastic, or metal vessel that can provide an aseptic environment for culturing cells.

The terms "primary culture" and "primary cells" refer to cells derived from intact or dissociated tissues or organ fragments. A culture is considered primary until it is passaged (or subcultured) after which it is termed a "cell line" or a "cell strain." The term "cell line" does not imply homogeneity or the degree to which a culture has been characterized. A cell line is termed "clonal cell line" or "clone" if it is derived from a single cell in a population of cultured cells. Primary cells can be obtained directly from a human or animal adult or fetal tissue, including blood. The primary cells may comprise a primary cell line, or such as, but not limited to, a population of muscle satellite cells.

Culture Medium:

The stem cells are grown in vitro in an appropriate liquid nutrient medium, in the presence of a p38 pathway inhibitor at an effective dose. Generally, the seeding level will be at least about 10 cells/ml, more usually at least about 100 cells/ml and generally not more than about $10^5$ cells/ml, usually not more than about $10^4$ cells/ml. Cells may be cultured singly or in groups.

Various media are commercially available and may be used, including Ex vivo serum free medium; Dulbecco's Modified Eagle Medium (DMEM), RPMI, Iscove's medium, etc. The medium may be supplemented with serum or with defined additives. For example a medium may include 5%, 10%, 15% serum, as known in the art. Appropriate antibiotics to prevent bacterial growth and other additives, such as pyruvate (0.1-5 mM), glutamine (0.5-5 mM), 2-mercaptoethanol ($1$-$10 \times 10^{-5}$ M) may also be included. The medium may be any conventional culture medium, generally supplemented with additives such as iron-saturated transferrin, human serum albumin, soy bean lipids, linoleic acid, cholesterol, alpha thioglycerol, crystalline bovine hemin, etc., that allow for the growth of hematopoietic cells. In some circumstances, proliferative factors that do not induce cellular differentiation may be included in the cultures, e.g. c-kit ligand, LIF, and the like.

The cultured cells expanded by the methods of the invention can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention.

It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

Figure 5:
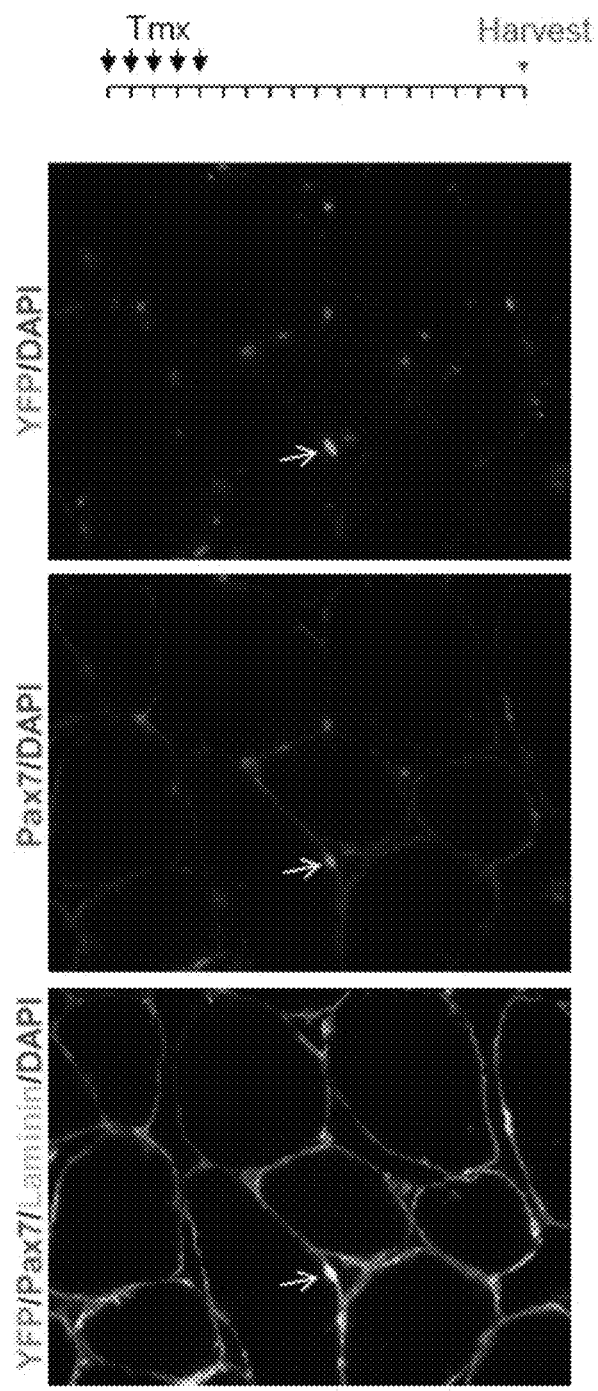
FIG. 5 SC-specific expression of a reporter protein YFP using the $Pax7^{creER}$ allele. The Tmx injection scheme is shown. The images demonstrate co-localization of Pax7 and YFP in cells (arrow) that are underneath the basal lamina. All $YFP^{+ve}$ cells were also $Pax7^{+ve}$, and no interstitial cells were found to be $YFP^{+ve}$.
Figure 6:
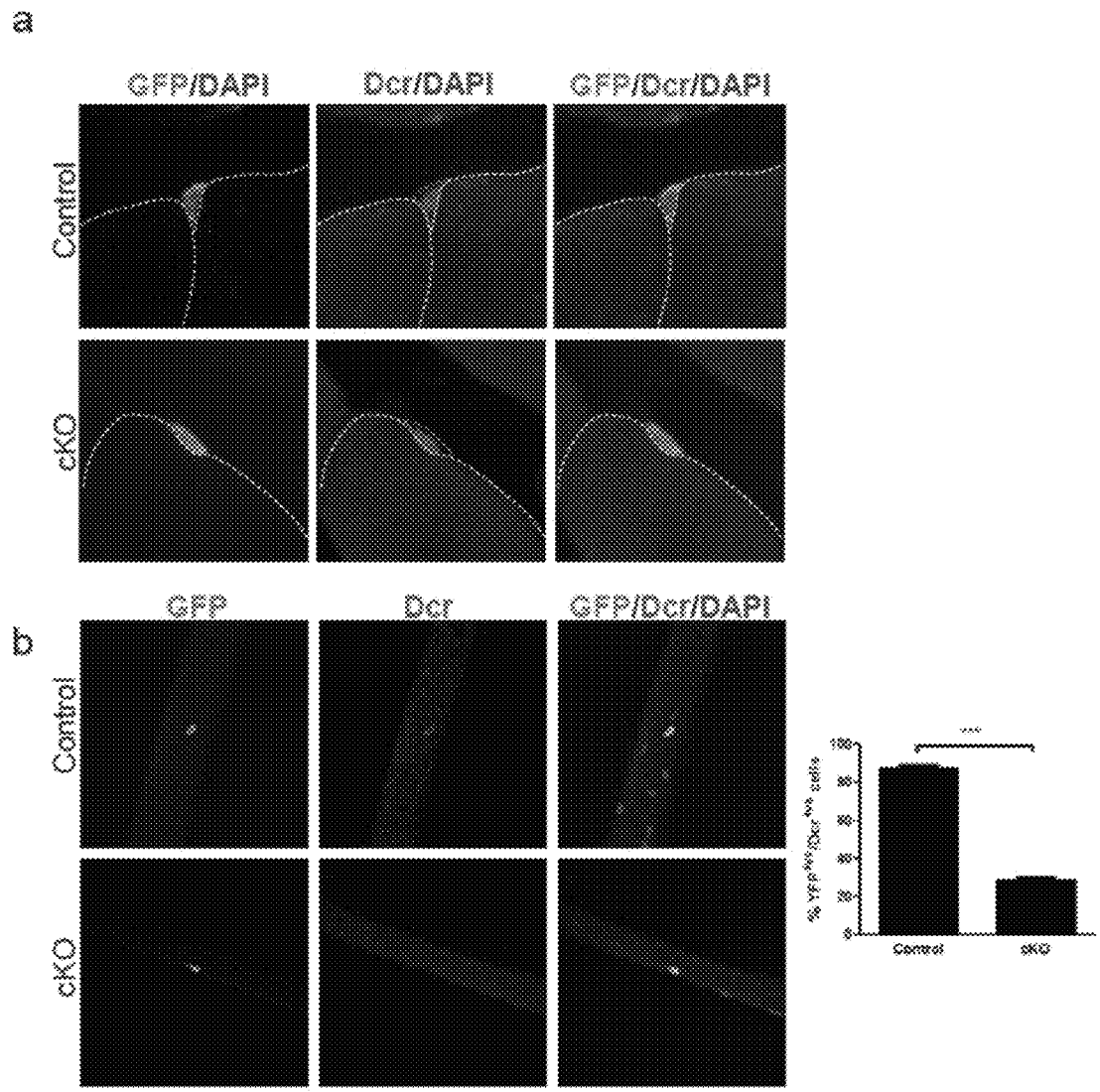
FIG. 6 Dicer protein is down-regulated in $YFP^{+ve}$ SCs of cKO mice six days after tamoxifen injection. A, Images of muscle sections from control and cKOmice that were stained for expression of GFP and Dicer using the same tamoxifen-injection scheme as in FIG. 1a. B, Images of freshly isolated single fiber explants from control and cKO mice that were stained for expression of GFP and Dicer using the same tamoxifen injection scheme as in FIG. 1a. Percentage of $YFP^{+ve}$ cells that were Dicer+ve was determined and shown on the right (n=3). (***P<0.001)
Figure 7:
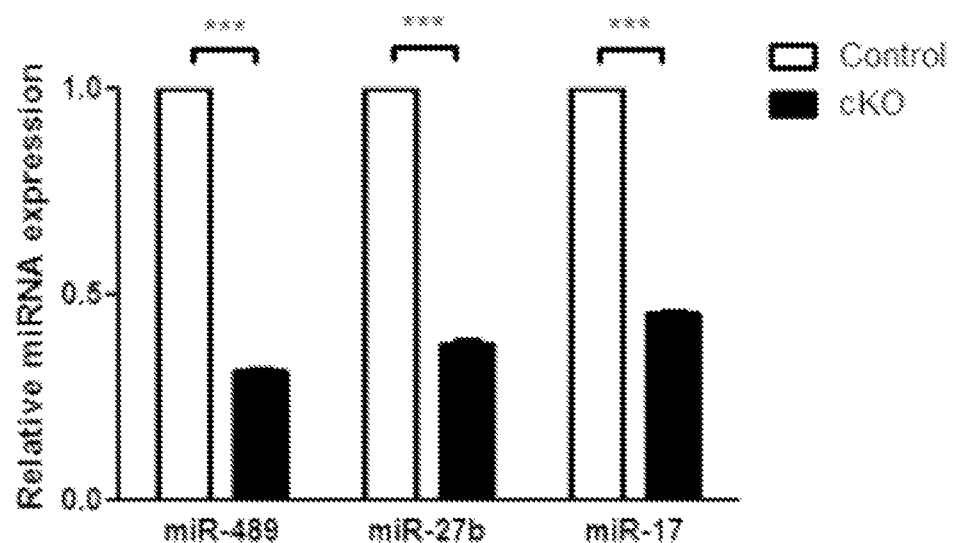
FIG. 7 miRNA levels are down-regulated in $YFP^{+ve}$ SC in cKOmice. $YFP^{+ve}$ SCs were sorted from control or cKO mice six days after first tamoxifen injection. qRT-PCR analyses of three miRNAs (miR-489, miR-27b and miR-17) were performed. Expression levels were normalized to snoRNA420. (***P<0.001)
Figure 8:
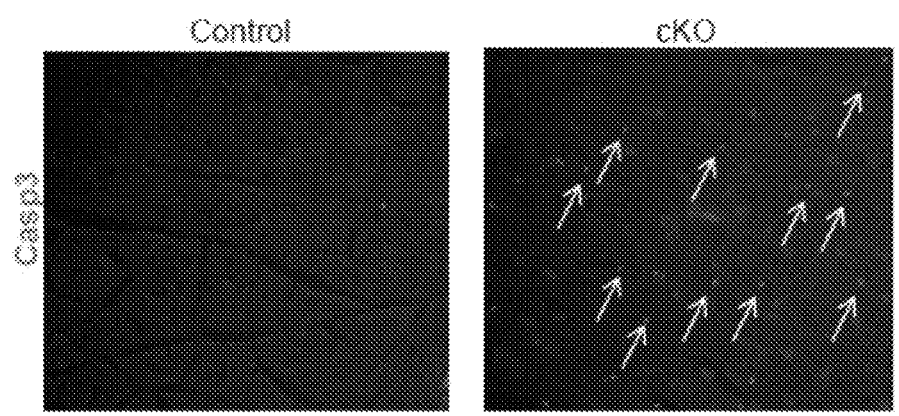
FIG. 8 Widespread apoptosis in muscles of adult cKO mice. A, Widespread cleaved Caspase3 staining in mononuclear cells (arrows) was found in muscles (TA muscle is shown) from cKO mice but not in control. A representative image of 3 independent experiments is shown. B, $Pax7^{+ve}$ SCs associated with freshly isolated single fibers from cKO mice were found to be positive for cleaved Caspase3 staining when analyzed at the same time point as in FIG. 1c. $Pax7^{+ve}$ SCs from control mice were $Casp3^{-ve}$.
Figure 8:
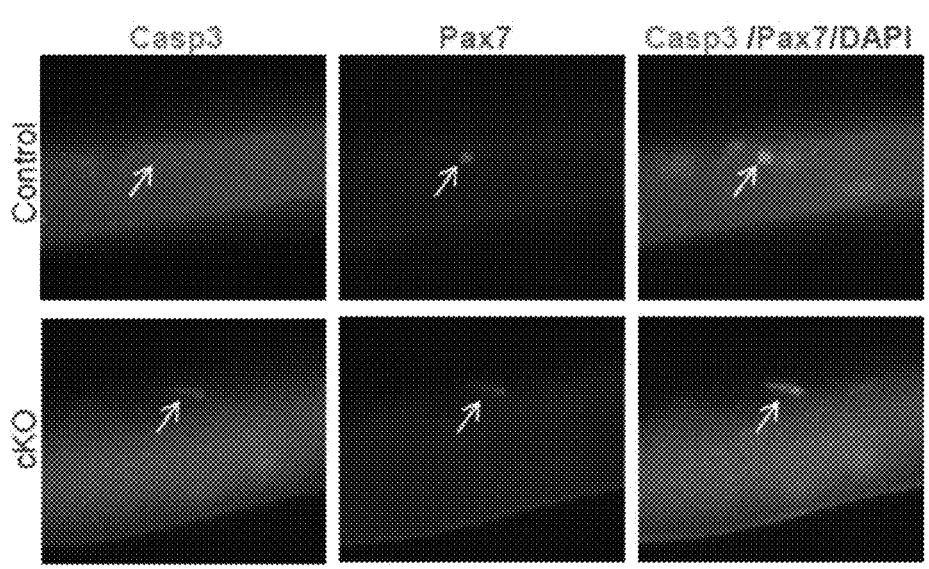

The miRNA pathway has been shown to be essential for stem-cell pluripotency, proliferation and differentiation (Yi et al. Nature 452, 225-229 (2008)) (Tiscornia, G. & Izpisua Belmonte, J. C., Genes Dev. 24, 2732-2741 (2010)). To understand whether adult quiescent stem cells are under active post-transcriptional control by miRNAs, we conditionally ablated the miRNA processing enzyme Dicer in adult muscle stem cells, or satellite cells, using a mouse strain that expresses a satellite-cell-specific, tamoxifen-inducible Cre/loxP system (Nishijo, K. et al., FASEB J. 23, 2681-2690 (2009)) (FIG. 5) and is homozygous for a floxed Dicer allele (Harfe et al. Proc. Natl Acad. Sci. USA 102, 10898-10903 (2005)) and a Cre-dependent yellow fluorescent protein (YFP) Reporter (Srinivas, S. et al., BMC Dev. Biol. 1, 4 (2001)). Six days after the first tamoxifen injection to this conditional knockout strain, Dicer protein and miRNA levels were significantly downregulated in YFP-positive satellite cells (P<0.001; FIGS. 6 and 7). Notably, in conditional knockout mice we detected YFP-positive satellite cells that had spontaneously exited quiescence and entered the cell cycle (FIG. 1a, b). In control mice, less than 1% of YFP-positive satellite cells were Ki67-positive at this time. These observations suggest that an intact miRNA pathway is essential for the maintenance of satellite-cell quiescence. Deletion of Dicer also led to apoptosis of proliferating satellite-cell progeny FIG. 1c, d and FIG. 8). Together, these experiments demonstrate the essential role of miRNAs in the maintenance of satellite-cell quiescence and in the survival of proliferating myogenic progenitors.

Figure 9:
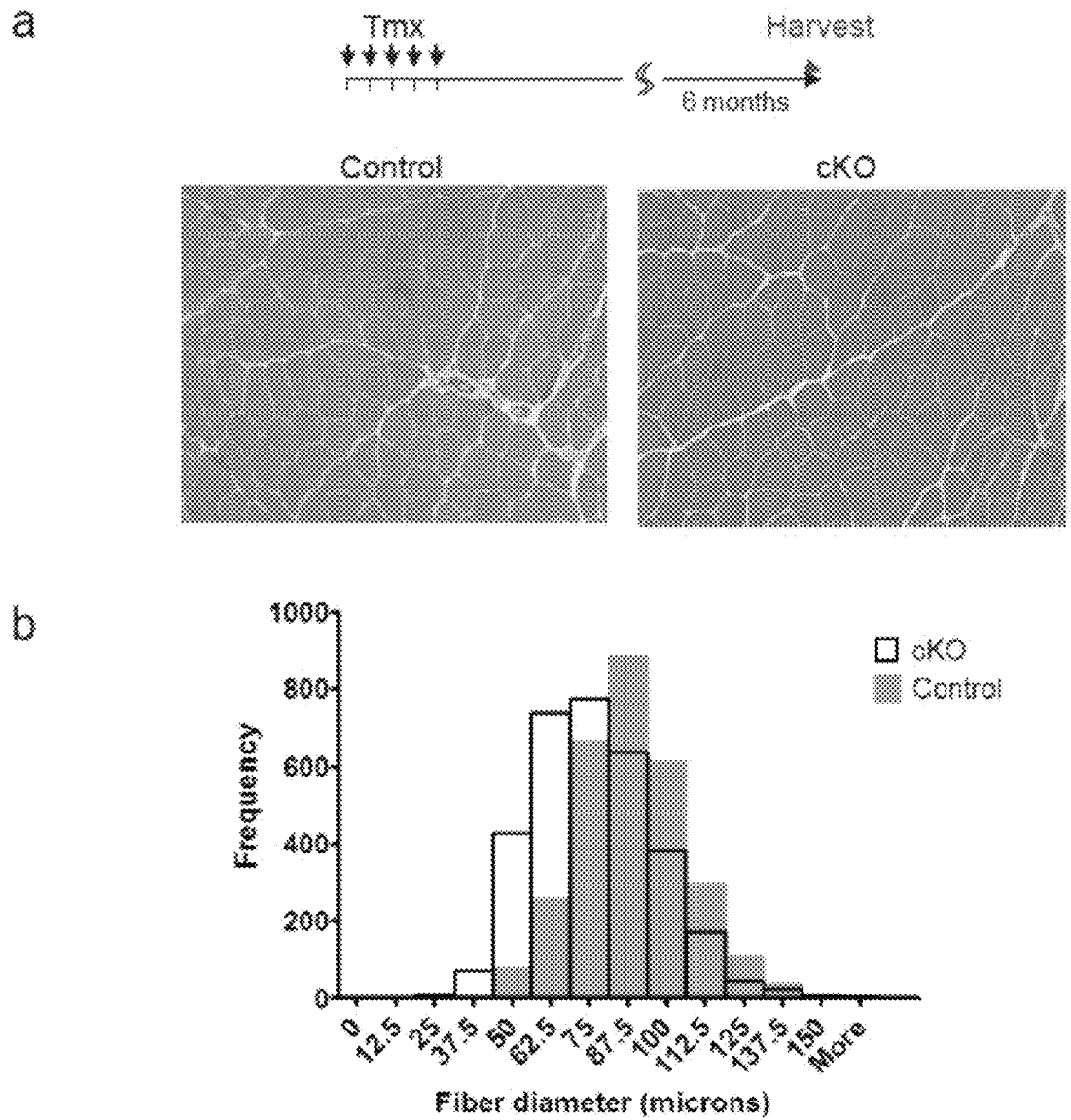
FIG. 9 Mild chronic atrophy in SC-depleted muscles. A, TA muscles appeared grossly normal in H&E stained sections six months after SC depletion in cKO mice compared to controls. A representative image of 3 independent experiments is shown. B, Quantitation of fiber diameter reveals mild fiber atrophy in the muscles of cKO mice compared to control animals.

To assess the impact of miRNA pathway disruption on satellite-cell homeostasis, we quantified the number of satellite cells using single-fibre explants and mononuclear cells that were isolated from uninjured muscles of conditional knockout mice 2 weeks after tamoxifen injections. We observed a marked reduction in satellite-cell number in the absence of Dicer (FIG. 1e, f). To confirm the functional loss of satellite cells, hindlimb muscles of tamoxifen-injected conditional knockout mice were injured to induce satellite-cell-mediated regeneration. Seven days after injury, very few regenerated fibers were observed in the conditional knockout mice, indicating severely impaired regeneration (FIG. 1g). Further analysis 6 months after injury revealed a marked reduction in the mass of injured muscles compared to the contralateral, uninjured muscles. By comparison, control mice exhibited a hypertrophic response after muscle injury (FIG. 1h). Consistent with the finding that adult muscle satellite cells have a low turnover rate (Morgan, J. E. & Partridge, T. A., Int. J. Biochem. Cell Biol. 35, 1151-1156 (2003)), uninjured muscle appeared in general to be normal 6 months after disruption of the Dicer gene (FIG. 9a). However, the loss of satellite cells resulted in mild muscle-fibre atrophy in conditional knockout animals over time (FIG. 9b).

Figure 2:
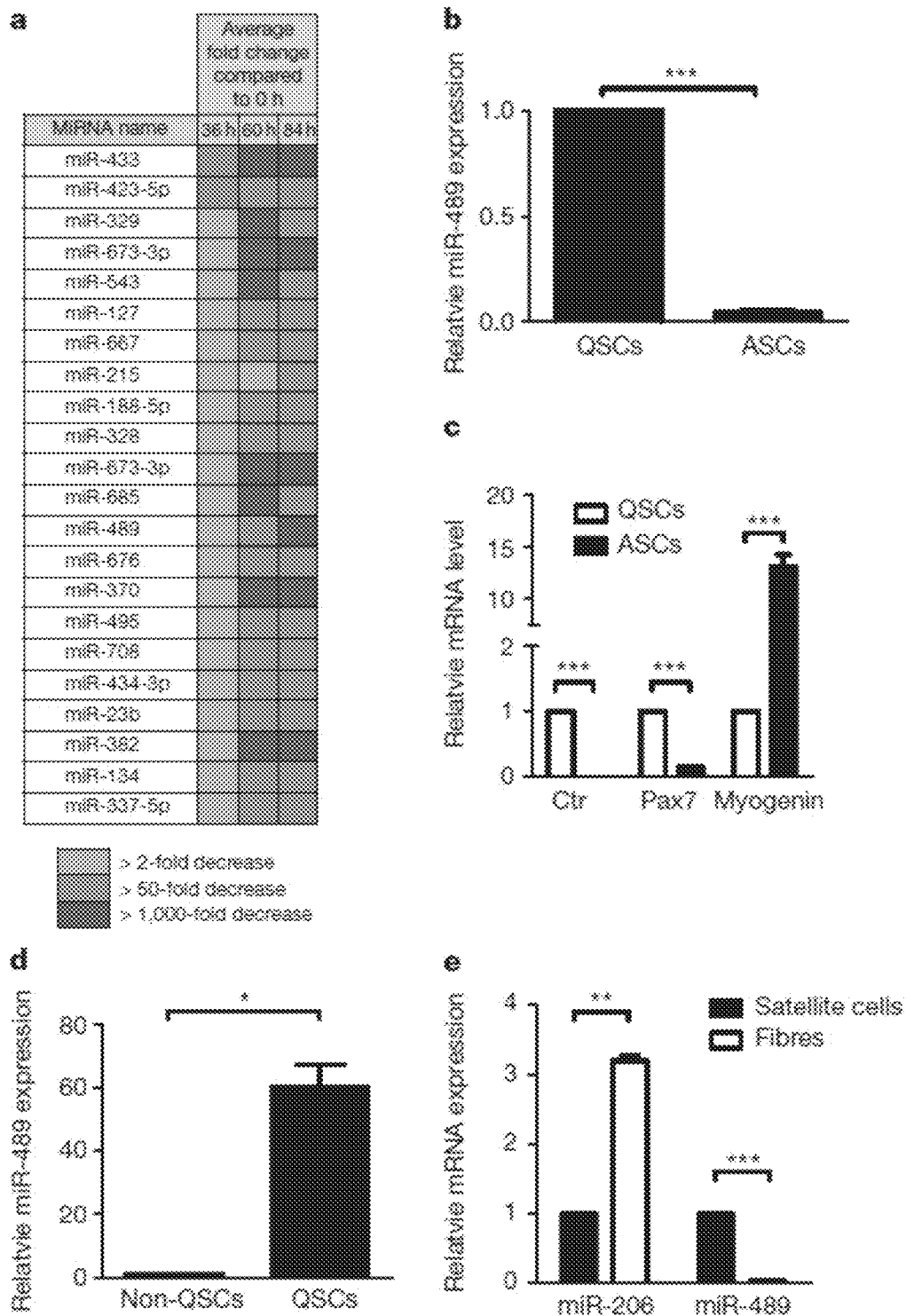
FIG. 2 miRNA expression in purified QSCs and ASCs. A, miRNA expression profiling during satellite-cell activation using qRT-PCR-based miRNA arrays. QSCs from uninjured muscles and ASCs from injured muscles at indicated time points were isolated by FACS (FIG. 10). QSC-specific mouse miRNAs are shown. B, qRT-PCR analysis of miR-489 transcript in QSCs and ASCs. Expression levels were normalized to snoRNA420. *P<0.001. C, qRT-PCR analysis of CTR, Pax7 and myogenin mRNA. Expression levels were normalized to glyceraldehyde-3-phosphate dehydrogenase (GAPDH). *P<0.001; **P<0.01. D, qRT-PCR analysis of miR-489 transcript in QSCs and all other mononuclear cells in hindlimb muscles. Expression levels were normalized to snoRNA420. *P<0.05. E, qRT-PCR analysis of miR-206 and miR-489 transcript in QSCs and single-fibre explants. Expression levels were normalized to snoRNA420. *P<0.001; P<0.01. All error bars indicate s.e.m.
Figure 10:
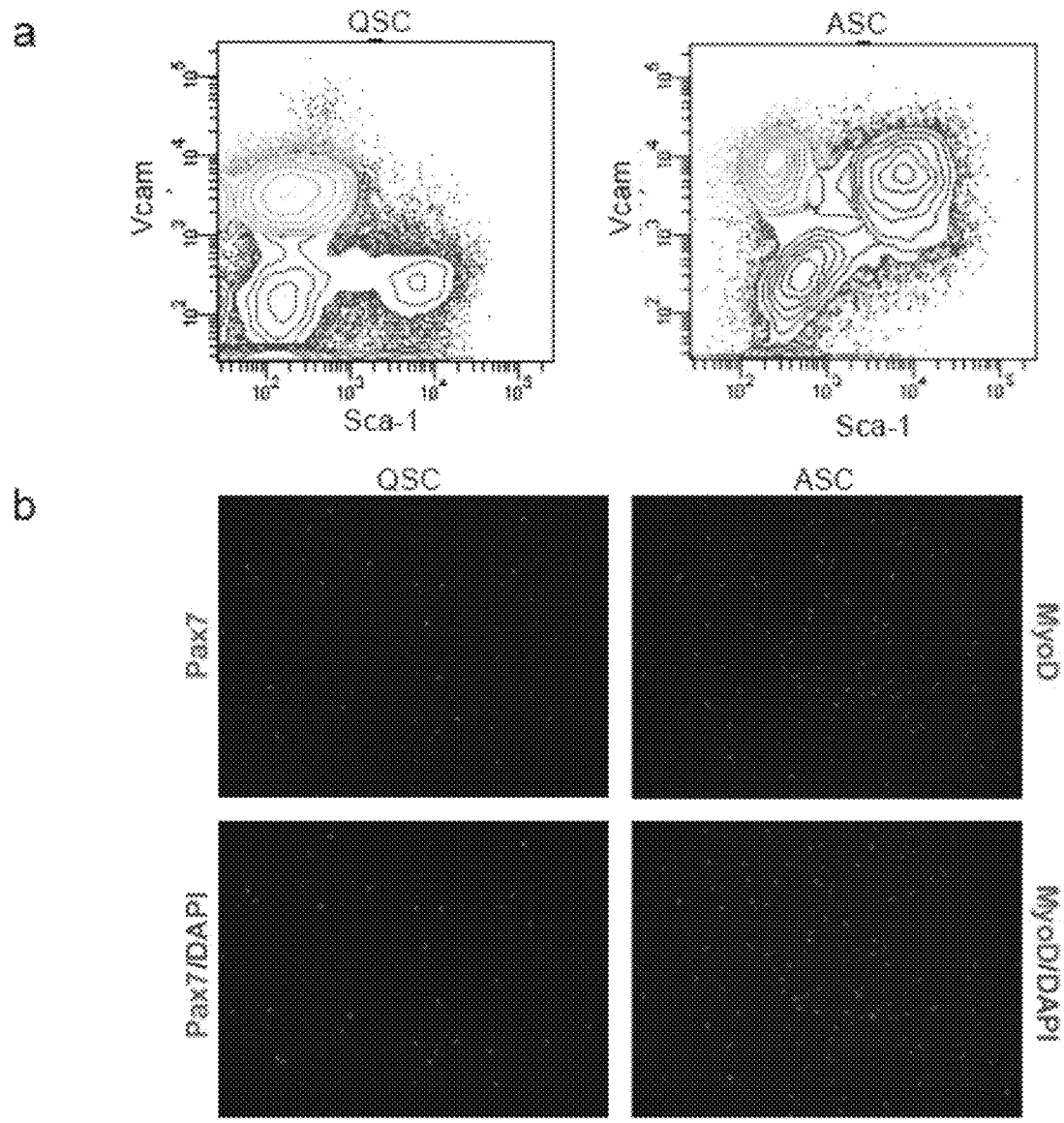
FIG. 10 QSCs and ASCs purification by FACS. A, Total mononuclear cells were prepared from hindlimb muscles. Cells were stained using antibodies against Vcam, CD31, CD45 and Sca1 and subjected to FACS first to obtain CD31⁻/CD45⁻cells (not shown) and then to obtain Vcam⁺/CD31⁻/CD45⁻/Sca1⁻ QSCs or ASCs (highlighted in orange). In uninjured muscles, the scheme Vcam+/CD31−/CD45−/Sca1− marks Pax7+ve SCs exclusively. In injured muscles, the scheme Vcam+/CD31−/CD45−/Sca1− marks proliferating myogenic progenitors. All other populations (CD31+, CD45+, Vcam−/CD31−/CD45−/Sca1+) or Vcam+/CD31−/CD45−/Sca1+) were sorted and stained using Pax7 or MyoD antibodies. None of these populations contained Pax7 or MyoD positive cells. B, FACS-purified QSCs and ASCs were plated and stained for the expression of Pax7 or MyoD. 98.9% of plated sorted cells are Pax7+ve (QSCs). A representative example of 6 independent experiments is shown. 93.9% of plated sorted cells are positive for MyoD (ASCs). A representative example of 3 independent experiments is shown.
Figure 11:
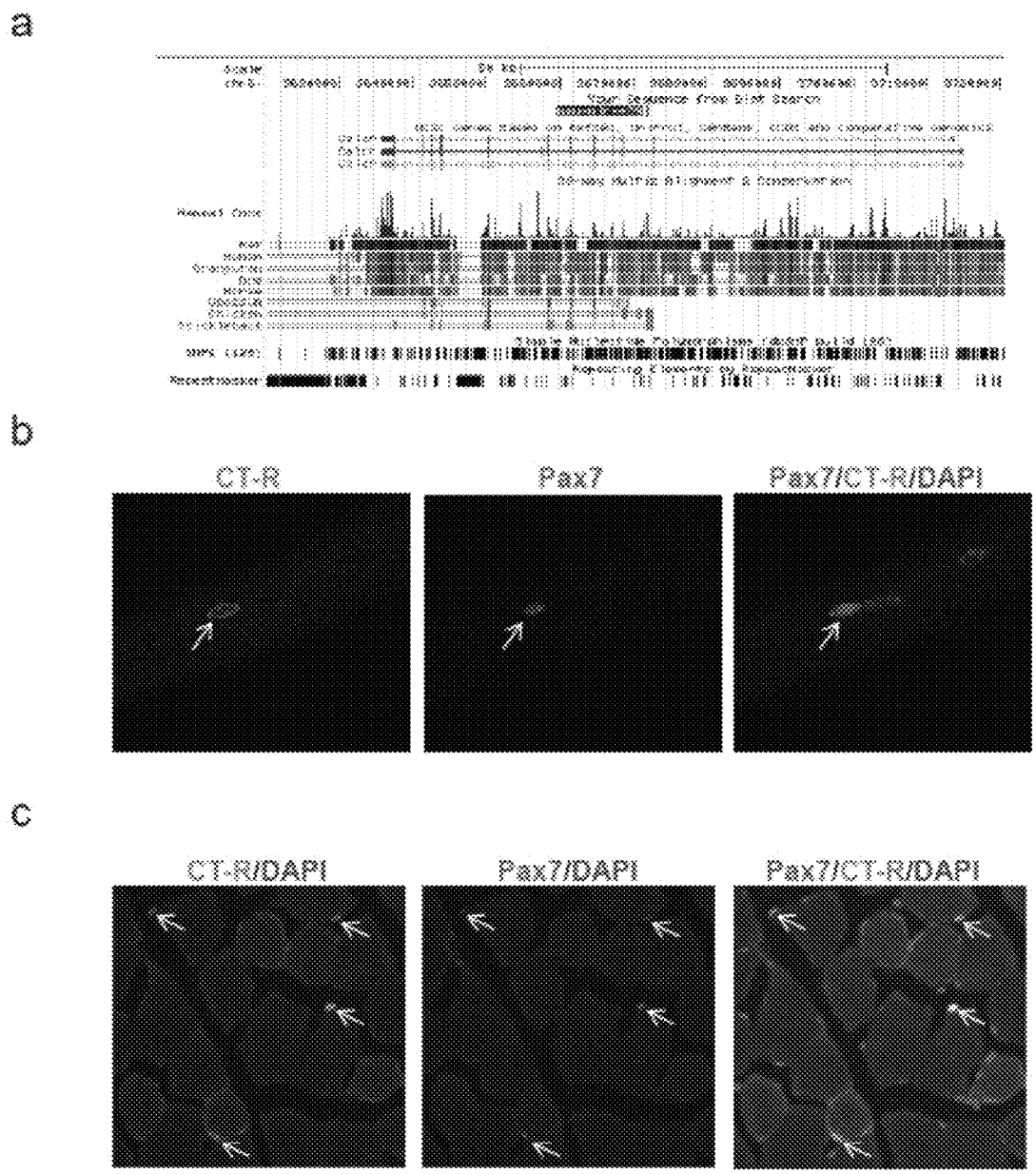
FIG. 11 Genomic localization of miR-489 and expression of CT-R in SCs. A, miR-489 is situated in intron 4 of the Calcitonin Receptor (CT-R) gene, illustrated using UCSC genome browser. B, Co-localization of CT-R and Pax7 in SCs on a freshly isolated muscle fiber (arrow). C, Co-localization of CT-R and Pax7 in SCs in an uninjured muscle cryosection. All CT-R+ve cells observed were found to be Pax7+ve (arrows).

As the disruption of Dicer caused satellite cells to break quiescence and enter the cell cycle, we were interested in defining the role of specific miRNAs in maintaining the quiescent state. Quantitative real-time polymerase-chain-reaction (qRT-PCR)-based miRNA microarray analysis of highly purified quiescent satellite cells (QSCs) and activated satellite cells (ASCs) (FIG. 10) revealed that 351 miRNAs were differentially regulated during satellite-cell activation. Of these, 22 were highly expressed in the quiescent state and markedly downregulated after satellite-cell activation (FIG. 2a). Among the 22 quiescence-specific miRNAs, we focused on miR-489 because it is evolutionarily conserved among species (Friedman, R. C., Farh, K. K., Burge, C. B. & Bartel, D. P., Genome Res. 19, 92-105 (2009)) and because it resides in intron 4 of the gene encoding calcitonin receptor (the Ctr gene; also known as Calcr) (FIG. 11a), which is highly expressed in QSCs (FIG. 11b, c) and has previously been shown to regulate satellite-cell quiescence (Fukada, S. et al., Stem Cells 25, 2448-2459 (2007)). Previous reports have suggested that intronic miRNAs co-express with host genes to co-regulate similar pathways (van Rooij, E. et al., Science 316, 575-579 (2007)). The quiescence-specific expression of miR-489 and CTR was verified by qRT-PCR analysis (FIG. 2b, c). To determine whether miR-489 is specifically expressed in QSCs, we performed qRT-PCR analysis of isolated satellite cells and other mononuclear cell populations from uninjured muscle. As expected from the expression pattern of CTR (FIG. 11c), miR-489 was highly enriched in QSCs relative to multinucleate muscle fibers or other mononuclear cells in the muscle (FIG. 2d, e).

Figure 3:
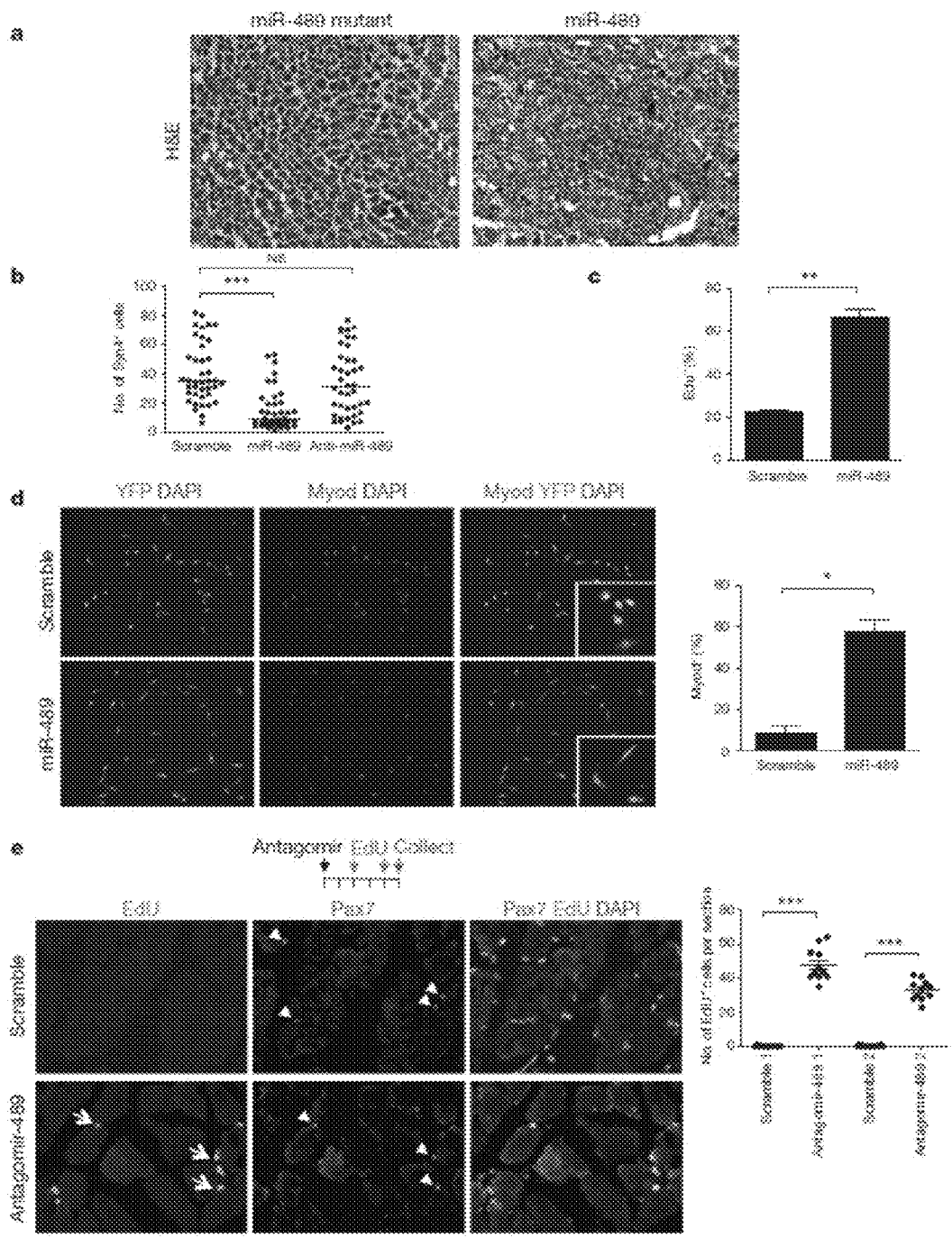
FIG. 3 miRNA-489 regulates satellite-cell quiescence. A, Hindlimb muscles were electroporated with either miR-489 expression plasmid (right) or a control miR-489 mutant plasmid (left). Muscles were collected 6 days later and haematoxylin and eosin staining was performed on cryosections. A representative image of three independent replicates is shown. B, miR-489 or anti-miR-489 was overexpressed in fibre-associated satellite cells. Three days after transfection, the number of syndecan-4-positive (Syn4) satellite-cell progeny was quantified. *P<0.001; NS, not significant. C, In studies such as those in B, EdU was added to the medium at the time of miR-489 (or control) transfection and the percentage of Syn41 cells that were EdU-negative (EdU⁻) was determined after 3 days. P<0.01. D, Left, FACS-sorted QSCs from $Pax7^{creER/+}$; $ROSA^{eYFP/+}$ mice were plated and transfected with miR-489 and analysed for Myod expression 48 h later. Right, quantification of the percentage of YFP-positive cells that were Myod-negative (Myod⁻). Nuclei were stained with DAPI. *P<0.05. E, Left, satellite-cell activation in vivo, as determined by EdU incorporation, was assessed in muscles in which miR-489 was inhibited by the systemic injection of a cholesterol-conjugated anti-miR-489 oligonucleotide (antagomir-489) or a scrambled antagomir (scramble). Pax7 EdU double-positive (arrows) and Pax7-positive cells (arrowheads) are highlighted. Right, quantitation of the number of EdU-positive (EdU⁺) cells on cryosections. Two representative replicates of four independent experiments are shown (nuclei were stained with DAPI). ***P<0.001. All error bars indicate s.e.m.
Figure 12:
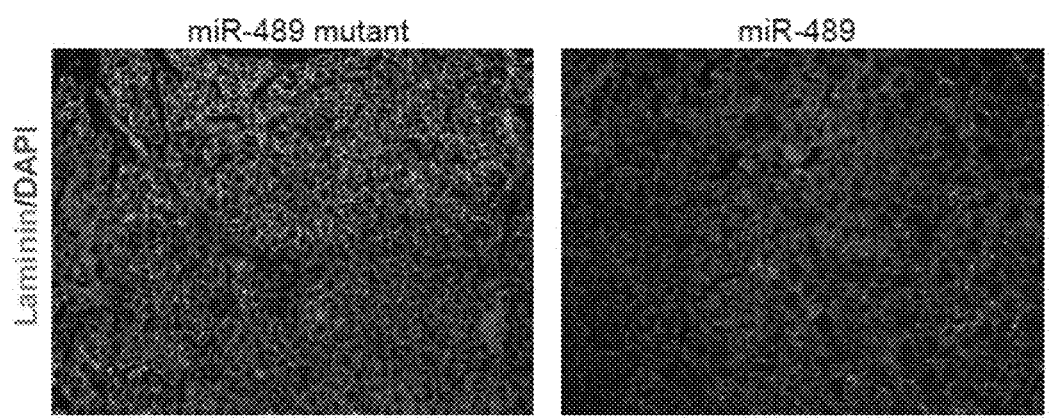
FIG. 12 Impairment of muscle regeneration by miR-489 overexpression. A, Hindlimb muscles were electroporated with either a mutant or control miR-489 expression plasmid. Muscles were harvested 6 days later and cryosections were immunostained with a laminin antibody. Nuclei were stained with DAPI. A representative image of 3 independent experiments is shown. B, Total RNA was extracted from TA muscles electroporated with a mutant or control miR-489 expression plasmid. Muscles were harvested at day 4 or day 6 after electroporation. miR-489 expression levels are shown by qRT-PCR analysis. Expression levels were normalized to snoRNA420 (n=3). (**P<0.01; *P<0.05)
Figure 12:
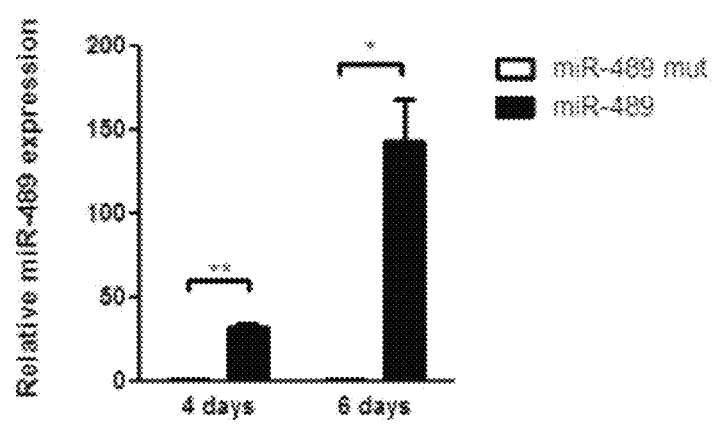

To test whether a sustained expression of miR-489 could lead to an impairment of muscle regeneration by suppressing satellite-cell activation, an miR-489 expression plasmid was electroporated into hindlimb muscles in vivo. qRT-PCR analysis revealed a high level of miR-489 expression in tibialis anterior muscles electroporated with miR-489 plasmid compared with the level in controls (FIG. 12b). Six days after electroporation, control muscles exhibited normal regeneration, whereas muscles expressing miR-489 exhibited a severe defect in regeneration (FIG. 3a and FIG. 12a).

To test the hypothesis that overexpression of miR-489 suppresses muscle regeneration by maintaining satellite-cell quiescence and suppressing activation, we overexpressed miR-489 or anti-miR-489 in fibre-associated QSCs ex vivo. Using syndecan 4 as a satellite-cell marker on fiber explants (Olguin, H. C. & Olwin, B. B., Dev. Biol. 275, 375-388 (2004)) (Tanaka, K. K. et al. Cell Stem Cell 4, 217-225 (2009)), we quantified the number of satellite cells on fibers 3 days after transfection. Satellite cells treated with anti-miR-489 exhibited similar proliferative activity as control satellite cells, whereas satellite cells treated with miR-489 exhibited markedly reduced proliferation (and no evidence of apoptosis) (FIG. 3b). Furthermore, fewer than 50% of the cells treated with miR-489 progressed through a single round of cell division over the course of the experiment as determined by 5-ethynyl-2'-deoxyuridine (EdU) labelling (FIG. 3c). To test whether miR-489 regulates satellite-cell quiescence in a cell autonomous manner, we used myogenic differentiation 1 (Myod; also known as Myod1) expression as an indicator of satellite-cell activation (Zammit, P. S., Partridge, T. A. & Yablonka-Reuveni, Z., J. Histochem Cytochem 54, 1177-1191 (2006)) and quantified the percentage of satellite cells expressing Myod 48 h after miR-489 transfection. Consistent with the fibre-explant experiment, miR-489 suppressed satellite-cell activation (FIG. 3d). Together, these experiments demonstrate that miR-489 regulates satellite-cell quiescence in a cell-autonomous manner and that overexpression of a single miRNA is sufficient to prolong the quiescent state and delay QSC activation, resulting in an impairment of regeneration in vivo.

Figure 13:
FIG. 13 Systemic delivery of antagomir-489 reduces miR-489 expression level in SCs in vivo. SCs were isolated from mice that were injected with antagomirs (scramble antagomir or antagomir targeting miR-489). qRT-PCR analysis of miR-489 transcript in SCs. Expression levels were normalized to snoRNA420. (*P<0.001; P<0.01; ns: not significant)

Next, we tested whether inhibition of miR-489 could result in the spontaneous activation of QSCs, which rarely divide in the absence of any activating stimuli (Morgan, J. E. & Partridge, T. A., Int. J. Biochem. Cell Biol. 35, 1151-1156 (2003)). Cholesterol-conjugated 'antagomirs' (Krutzfeldt, J. et al., Nature 438, 685-689 (2005)) that specifically target miR-489, or control scrambled antagomirs, were delivered systemically to adult mice. Four days after a single antagomir injection, miR-489 transcript levels decreased precipitously (FIG. 13). In contrast to the control mice, which were injected with scrambled antagomirs, mice injected with anti-miR-489 antagomirs exhibited spontaneous activation of QSCs that incorporated EdU (FIG. 3e). Notably, inhibition of one quiescence-specific miRNA, miR-489, was sufficient to induce QSCs to break quiescence and progress through the cell cycle in uninjured muscle.

Figure 14:
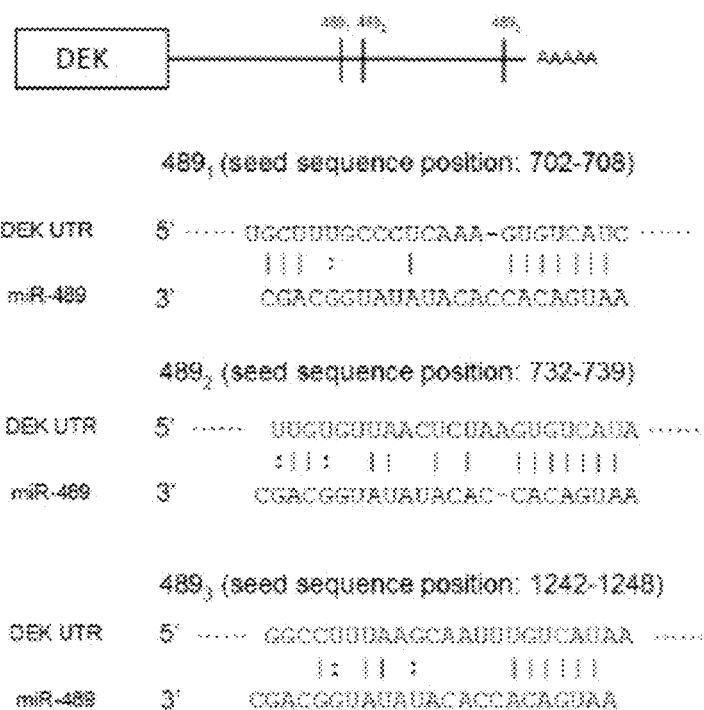
FIG. 14 Putative miR-489 target sites in the 3'UTR of DEK. TargetScan predicted three potential miR-489 target sites in the 3'UTR of DEK. Sites of point mutations made to abolish the potential pairing at the seed regions are shown in red. SEQ ID NOs: 1-3, 2, 4, and 2 from top to bottom.

The observation that inhibition of miR-489 induced satellite-cell activation and proliferation prompted us to test whether miR-489 functions to suppress one or more key regulators of proliferation, thereby maintaining the quiescent state. We used the bioinformatics tool TargetScan to search for miR-489 target genes that contain putative miR-489 target sites in their 3' untranslated regions (3' UTRs) (Friedman, R. C., Farh, K. K., Burge, C. B. & Bartel, D. P., Genome Res. 19, 92-105 (2009)). Among the 86 targets predicted by TargetScan, the transcript with the highest context score (Grimson, A. et al. Mol. Cell 27, 91-105 (2007)) was the oncogene Dek (FIG. 14), which has been shown to be induced in tumour cells and to regulate cell proliferation and messenger RNA splicing (Khodadoust, M. S. et al., Cancer Res. 69, 6405-6413 (2009) (Soares, L. M., Zanier, K., Mackereth, C., Sattler, M. & Valcarcel, J., Science 312, 1961-1965 (2006)). We analysed the temporal expression of Dek mRNA and protein during satellite-cell activation. Using paired box protein 7 (Pax7) as a marker of QSCs and Myod as a marker of ASCs (Zammit, P. S., et al., J. Cell Biol. 166, 347-357 (2004)) (Zammit, P. S. et al., J. Cell Sci. 119, 1824-1832 (2006)), we found that Dek protein was not expressed in QSCs but was strongly upregulated after satellite-cell activation both in fibre-explant studies ex vivo and in regeneration studies in vivo (FIG. 4a and FIG. 15a-c). Likewise, Dek mRNA levels were higher in ASCs compared to QSCs (FIG. 15d).

Figure 4:
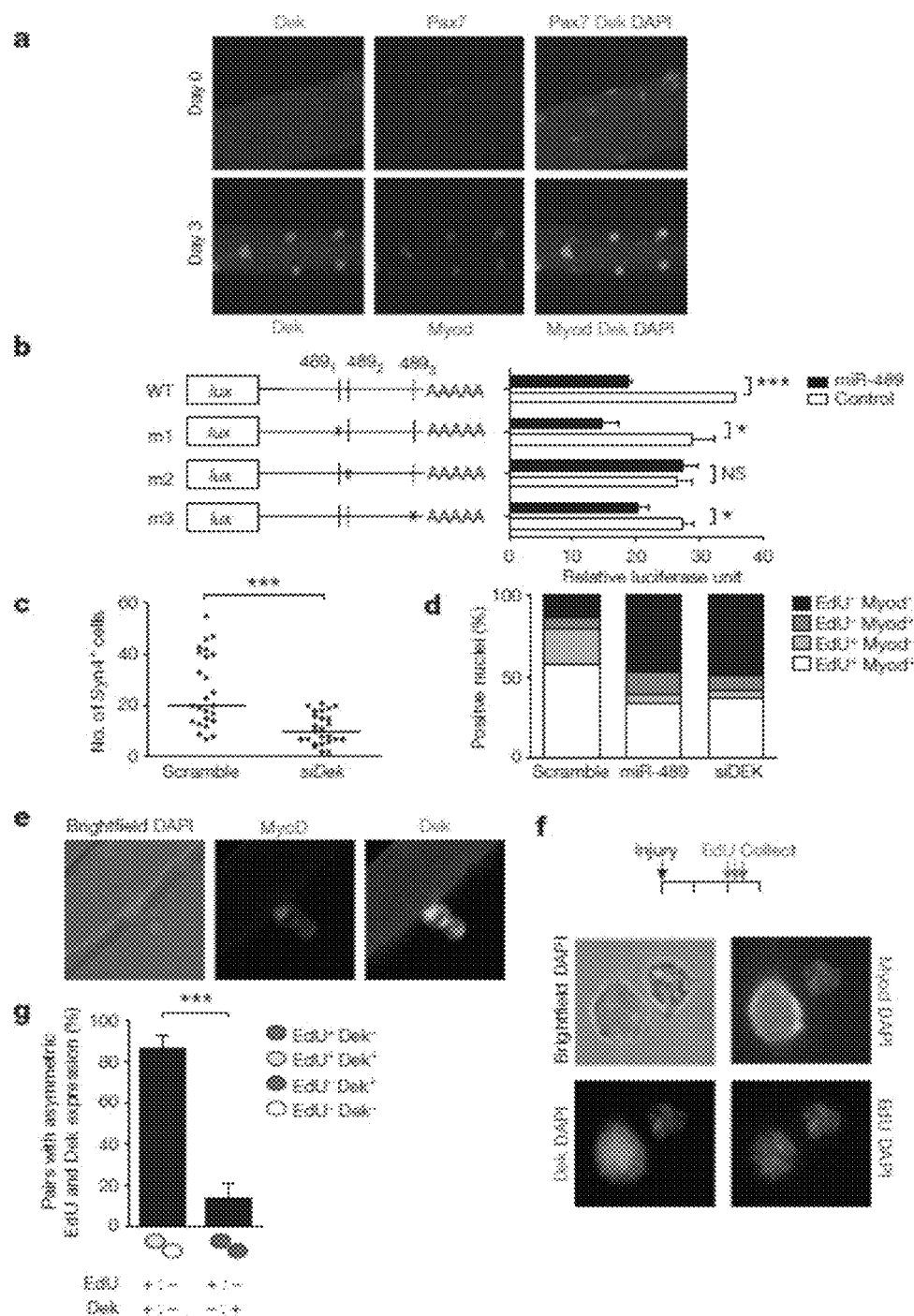
FIG. 4 Targeting of Dek mRNA by miR-489 and regulation of cell-fate decision of satellite-cell progeny by Dek. A, Co-localization of Dek and myogenic markers in fibre-associated satellite cells. Fibre explants were fixed immediately after isolation (Day 0) or cultured for 3 days in suspension and stained for expression of Pax7 and Dek, or Myod and Dek, as indicated. Nuclei were stained with DAPI. B, CMV-miR-489 was co-transfected into 293T cells with wild-type (WT) or mutant Dek 3' UTR constructs inserted after the stop codon of a luciferase gene. The Dek 3' UTR carries three putative miR-489 target sites ($489_1$, $489_2$ and $489_3$) (putative pairing as shown in FIG. 14). Schematics of wild-type and mutant constructs (m1, m2 and m3) are shown with the relative luciferase activities associated with each construct. ***P<0.001; *P<0.05; NS: not significant. C, Satellite cells in fibre explants were transfected with Dek short interfering RNA (siRNA) (siDek) and cultured for 3 days, and the satellite-cell progeny were quantified by syndecan 4 staining (n53). *P<0.001. D, FACS-purified QSCs were plated and transfected with miR-489 or siDek for 48 h. EdU was added to the medium at the same time as transfection. Cells were stained for EdU incorporation and Myod expression. Bar graphs show the proportion of cells expressing each marker under each condition. E, Dek asymmetrically localizes to one daughter after cell division. Fibre-associated satellite cells were cultured for 48 h and stained for expression of Myod and Dek. Nuclei were stained with DAPI. F, The timeline for injury, EdU injections and collection of cells is shown (top). Cells were stained for EdU incorporation to reveal nonrandom template-strand segregation and for Myod expression to reveal divergent cell fates. Dek co-segregates almost exclusively with the newly synthesized template strands. Images show a representative example of a cell pair exhibiting divergent cell fates with asymmetric segregation of template strands. Nuclei were stained with DAPI. G, Quantitative analysis of concordant and discordant asymmetries of Dek and EdU in asymmetric satellite-cell divisions in studies such as those in F. P<0.001. All error bars indicate s.e.m.
Figure 16:
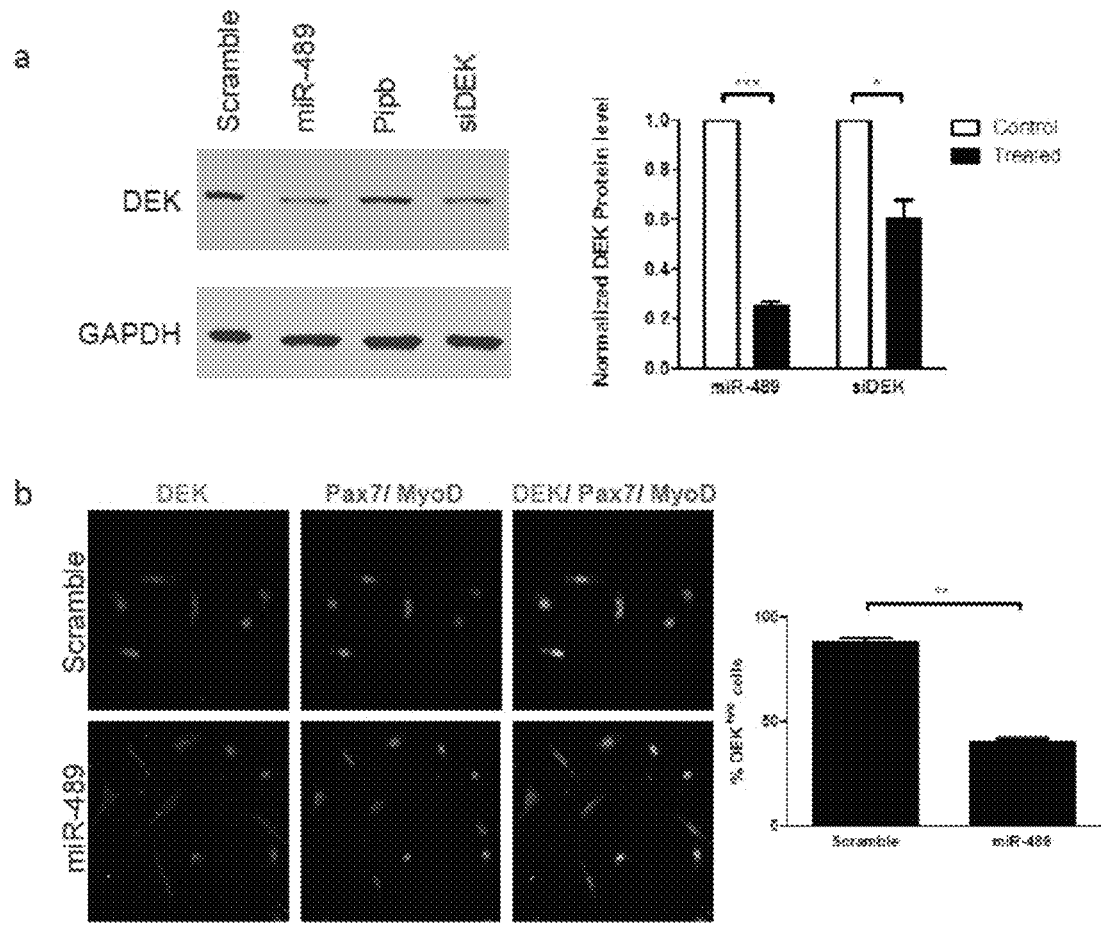
FIG. 16 miR-489 inhibits DEK expression. A, (Left) A western blot of DEK (and GAPDH as control) protein levels in proliferating C2C12 myoblasts transfected with scramble, miR-489, cyclophilin B (Pipb) or siRNA targeting DEK for 48 hours is shown. (Right) Quantitation of the western blot as shown in (A) (n=3). B, Freshly isolated QSCs were transfected with miR-489 or control oligonucleotides and stained for DEK 48 hours later. Quantitation of the percentage of DEK+ve SCs is shown on the right (n=3).

Dek protein was downregulated when QSCs or myoblasts were transfected with miR-489 (FIG. 16), suggesting that Dek is a direct target of miR-489. To test this directly, wild-type and mutant versions of the 3' UTR of Dek were cloned downstream of a luciferase reporter, and these reporter constructs were co-transfected with an miR-489 expression construct into 293T cells. The wild-type Dek 3' UTR was effectively downregulated by miR-489 (FIG. 4b). Although TargetScan analysis revealed three potential target sites for miR-489, a single site (m2) was sufficient to account for the suppression of reporter expression by miR-489 (FIG. 4b).

Figure 17:
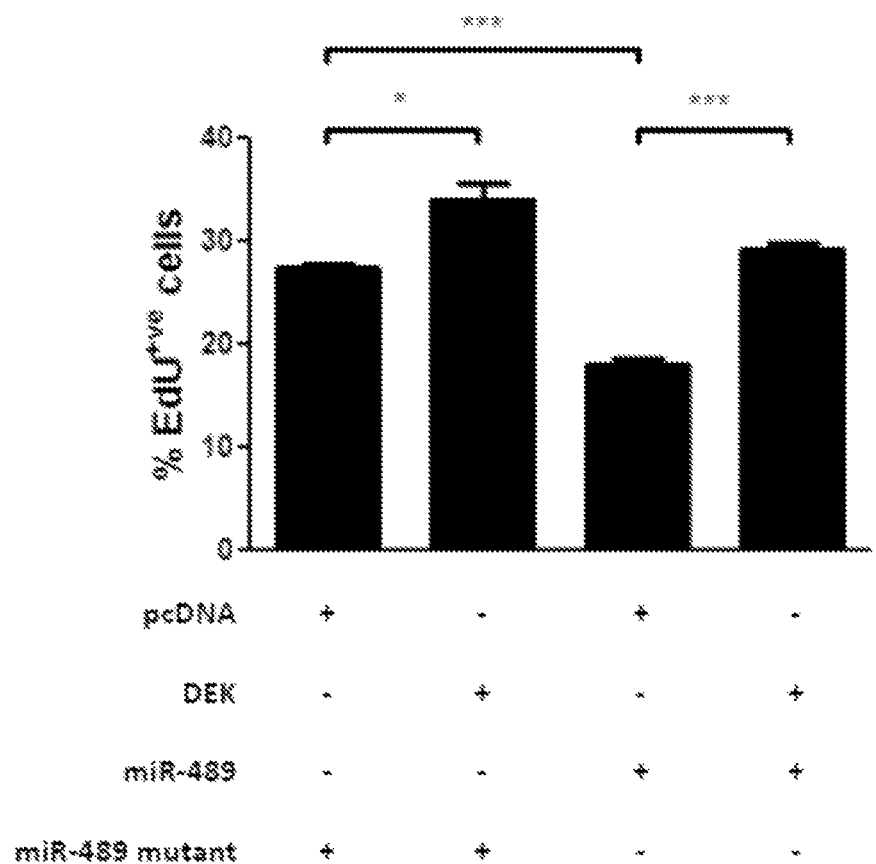
FIG. 17 DEK restores miR-489 dependent suppression of myoblast proliferation. Proliferating C2C12 myoblasts were transfected either a control plasmid (mutant miR-489 not targeting DEK and the reporter ZsGreen) or a plasmid expressing miR-489 (and the ZsGreenreporter). In each case, cells were co-transfected with a control plasmid (pcDNA) or a plasmid encoding a DEK without its 3'UTR. Only ZsGreen+ve cells were counted. Four hours after transfection, cells were pulsed with EdU at 44 hours and then harvested. Cells were fixed and assayed for EdU positivity. Quantitative analyses of the percentage of EdU+ve cells are shown (n=3). (***P<0.001; *P<0.05)

We next examined the role of Dek in satellite-cell quiescence and activation using a loss-of-function approach. Dek knockdown reduced satellite-cell proliferation (FIG. 4c) and prevented satellite-cell activation to the same degree as did miR-489 overexpression (FIG. 4d). The ability of Dek knockdown to phenocopy the effect of miR-489 overexpression suggests a central role of Dek in regulating satellite-cell exit from quiescence. To understand whether miR-489 overexpression suppresses proliferation by regulating Dek expression, we overexpressed miR-489 or miR-489 mutant with a Dek complementary DNA construct that lacks its 3' UTR in proliferating myoblasts. Overexpression of miR-489 alone reduced cell proliferation, whereas overexpression of Dek substantially increased cell proliferation independent of the expression of miR-489 or miR-489 mutant (FIG. 17). Together, these experiments suggest that Dek is an important target of miR-489 that is involved in the regulation of satellite-cell quiescence and activation.

Figure 15:
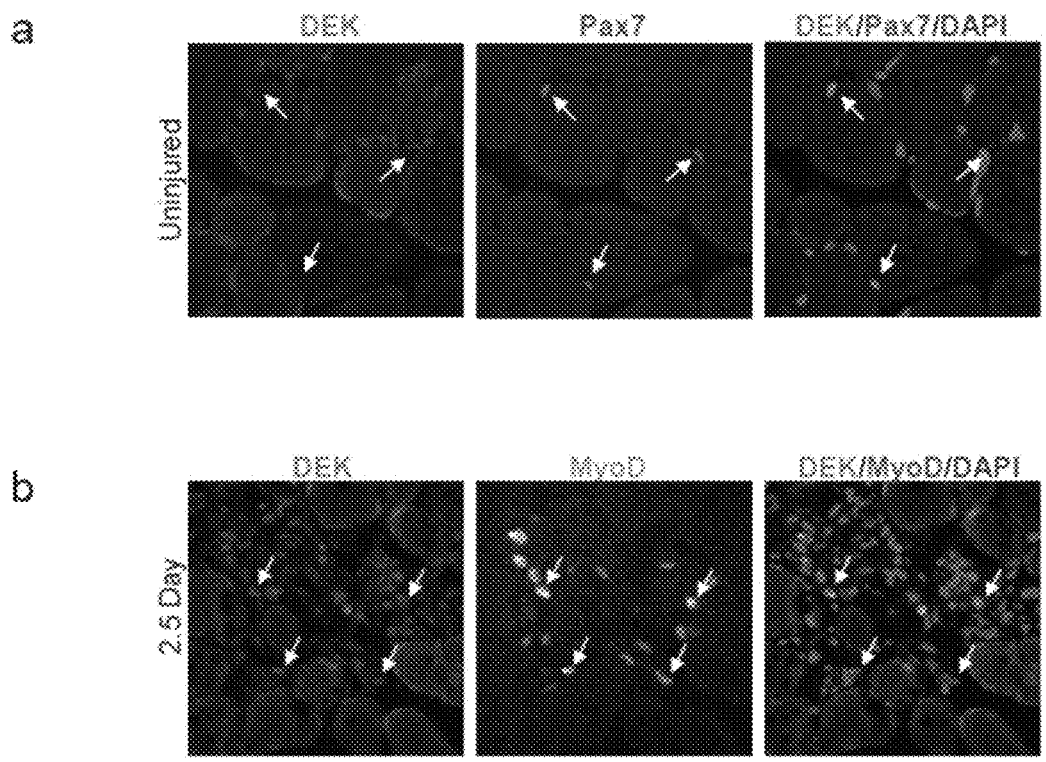
FIG. 15 DEK mRNA and protein expression during muscle regeneration in vivo. A, Uninjured TA muscles were cryosectioned and stained for expression of Pax7 and DEK. Pax7+ve cells are highlighted (arrows); these cells are DEK−ve. B, TA muscles were injured using $BaCl_2$ and allowed to recover for 2.5 days, cryosectioned and stained for expression of MyoD and DEK. Double positive cells are highlighted (arrows). C, TA muscles were injured using $BaCl_2$ and allowed to recover for 5.5 days or two weeks, cryosectioned and stained for expression of Pax7, MyoD and DEK. Arrows show Pax7+ve cells that are DEK−ve (and MyoD-ve). D, qRT-PCR analysis of DEK mRNA in freshly isolated QSCs and ASCs (n=3). (*P<0.05)
Figure 15:
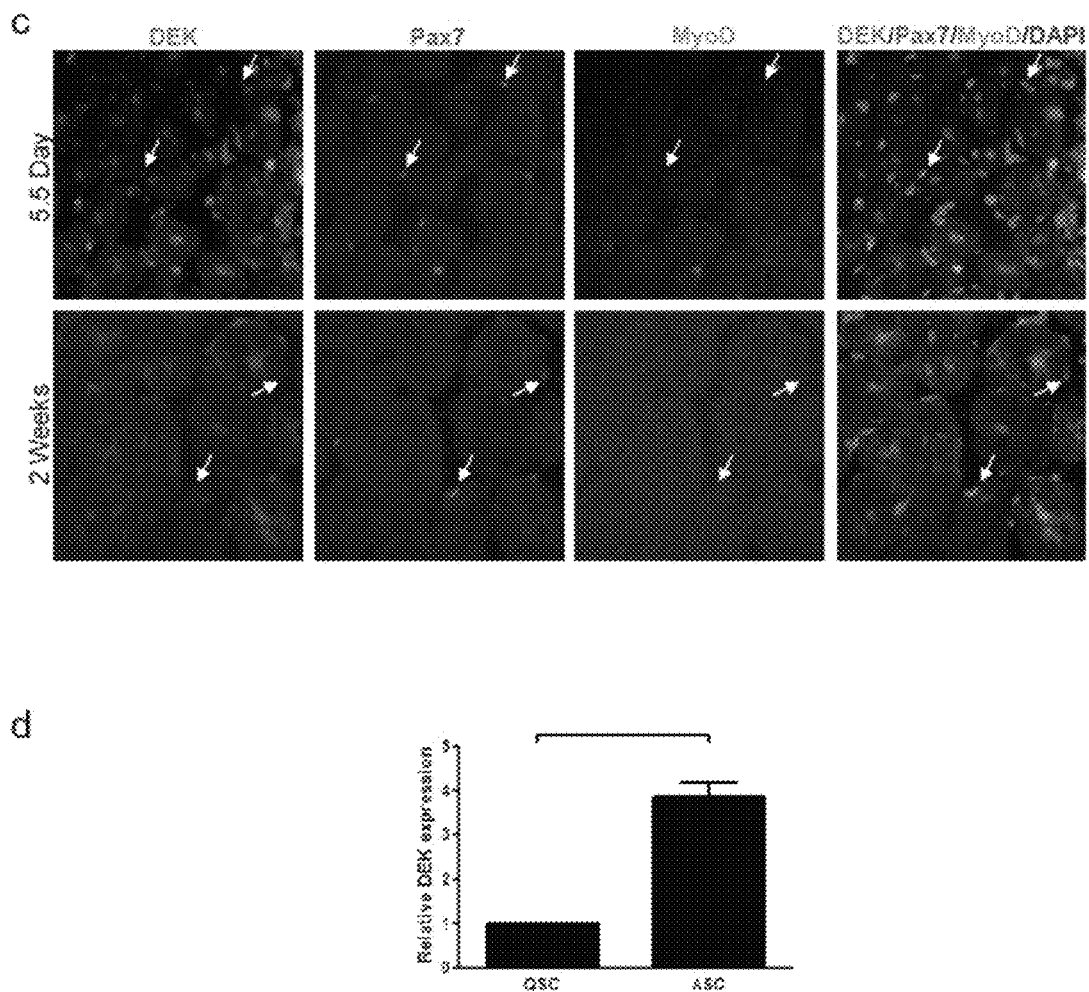
Figure 18:
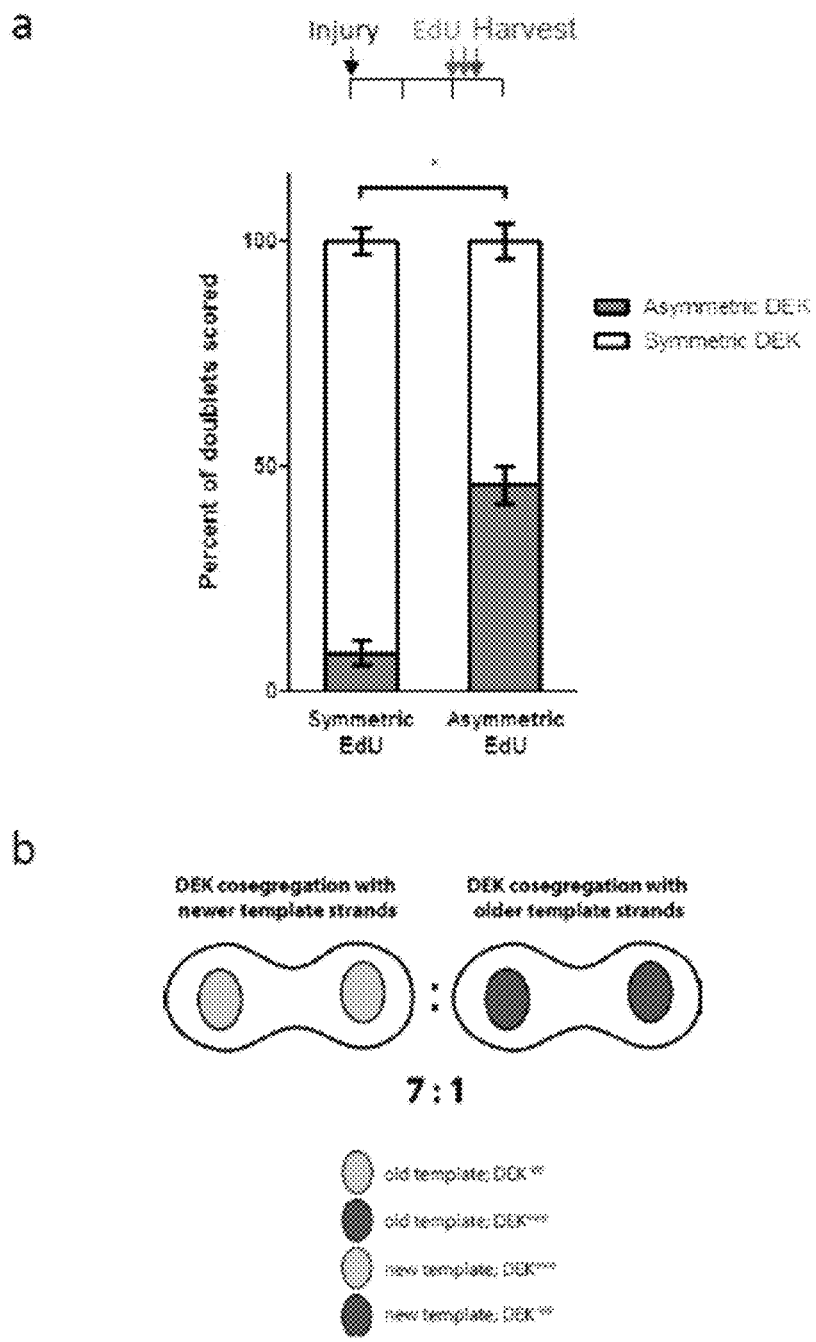
FIG. 18 Concordant asymmetry of DEK and EdU in SC division. A, The timeline for injury, EdU injections, and collection of cells is shown above. SC pairs were stained for EdU and DEK. Nearly half of cell pairs exhibiting asymmetric EdU labeling (non-random chromosome segregation (Shinin, V., Gayraud-Morel, B., Gomes, D. & Tajbakhsh, S., Nature Cell Biol. 8, 677-687 (2006))) displayed asymmetric DEK localization. Relatively few cell pairs exhibiting symmetric EdU labeling (random chromosome segregation) displayed the same asymmetric distribution of DEK protein. (*P<0.05). B, Schematic representation of DEK localization relative to template strand age in sister cell pairs that exhibit non-random chromosome segregation. DEK protein predominantly segregates with EdU-labeled, newer template strands by the ratio shown (7:1; n=50).

Although Dek expression was highly induced after satellite-cell activation, consistent with its role in proliferative expansion of the transit-amplifying myogenic progenitors, it was absent in self-renewed satellite cells after muscle injury in vivo (FIG. 15c). We therefore studied satellite-cell self-renewal in fibre explants ex vivo, in which the asymmetric expression of Myod by daughter cells heralds a divergent cell fate whereby the Myod-positive daughter progresses along the myogenic lineage and the Myod-negative daughter renews the satellite-cell population (Zammit, P. S., et al., J. Cell Biol. 166, 347-357 (2004)). Intriguingly, in such pairs, we observed asymmetric Dek expression, in which Dek expression coincided with Myod expression in the same daughter cell (FIG. 4e). This co-localization suggests that the Dek-positive daughter is destined for proliferative amplification as a progenitor and that the Dek-negative daughter is destined for self-renewal. To test whether the process of self-renewal is associated with the absence of Dek, we examined cells undergoing asymmetric division by analysing nonrandom chromosome segregation, a process that we and others have previously shown to distinguish the differentiating progenitor from the self-renewing stem cell (Conboy, M. J., Karasov, A. O., & Rando, T. A., PLoS Biol. 5, e102 (2007)) (Shinin, V., Gayraud-Morel, B., Gomes, D. & Tajbakhsh, S., Nature Cell Biol. 8, 677-687 (2006)). Consistent with the Myod asymmetry, we found that Dek was absent in the daughter cell inheriting chromosomes bearing older template DNA strands, an inheritance pattern that is characteristic of the self-renewing cell, whereas Dek was expressed in the daughter cell that is destined for proliferative amplification and differentiation (FIG. 4f, g and FIG. 18).

The finding that Dek is a key target of miR-489 in maintaining quiescence provides insight into the molecular pathways that regulate the quiescent state. These data demonstrate that the molecular regulation of quiescence is dependent on the expression of specific miRNAs and is integrated in the signalling network that regulates divergent fates of stem-cell progeny during asymmetric cell division.

METHODS SUMMARY

Single-Fiber Explants.

Extensor digitorumlongus (EDL) muscles were excised and digested in Collagenase II (500 units per ml in Ham's F10 medium) as previously described (Rosenblatt, J. D., Lunt, A. I., Parry, D. J. & Partridge, T. A., In vitro Cell Dev. Biol. Anim. 31, 773-779 (1995)). Fibers were then washed extensively and cultured in medium containing Ham's F10, 10% horse serum and 0.05% chick embryo extract. Every 24 h, 50% of the medium was replaced with Ham's F10 medium with 20% FBS. Extensor digitorum longus (EDL) fibers were cultured in suspension. Fixed fibers were stained and the number of satellite cells was quantified per fiber.

Satellite-Cell Isolation and Fluorescence-Activated Cell Sorting.

Hindlimb muscles were dissected and dissociated to yield a muscle suspension and digested with Collagenase II (500 units per ml; Invitrogen) in Ham's F10 medium with 10% horse serum (Invitrogen) for 90 min. Digested fiber suspensions were washed and digested further with Collagenase II (100 units per ml) and Dispase (2 units per ml; Invitrogen) for 30 min. Digested fiber suspensions were triturated and washed further to yield a mononuclear-cell suspension for cell-surface staining for fluorescence-activated cell sorting (FACS). Mononuclear cells were stained with Vcam-biotin (clone 429; BD Bioscience), CD31-APC (clone MEC 13.3; BD Bioscience), CD45-APC (clone 30-F11; BD Bioscience) and Sca-1-Pacific-Blue (clone D7; Biolegend) at 1:75. Streptavidin-PE-cy7 was used to amplify the Vcam signal (BD Biosciences, 1:75). Cell sorting was performed using a BD FACSAria II or BD FACSAria III cell sorter equipped with 488-nm, 633-nm and 405-nm lasers. The machine was optimized for purity and viability, and sorted cells were subjected to FACS analysis directly after sorting to ensure purity. A small fraction of sorted cells was plated and stained for Pax7 and Myod to assess the purity of the sorted population purity.

METHODS

Animals

C57BL/6, ROSA$^{eYFP/eYFP}$ and Dcr$^{loxP/loxP}$ mice were obtained from Jackson Laboratory (Harfe et al., Proc. Natl Acad. Sci. USA 102, 10898-10903 (2005)) (Srinivas, S. et al., BMC Dev. Biol. 1, 4 (2001)). Pax7$^{7creER}$ Cre mouse was provided by C. Keller. Tamoxifen injection for Cre recombinase activation was performed as described previously (Nishijo, K. et al., FASEB J. 23, 2681-2690 (2009)). Unless indicated, all control animals used in this study carried the genotype Pax7$^{+/+}$; Dcr$^{loxP/loxP}$; ROSA26$^{+/+}$ and all conditional knockout strain animals carried the genotype Pax7$^{CreER/+}$; Dcr$^{loxP/loxP}$; ROSA26$^{+/+}$. In FIG. 1a-d and FIG. 7, control and conditional knockout strain animals are mice that carry the genotypes Pax7$^{CreER/+}$; Dcr$^{+/+}$; ROSA26$^{eYFP/eYFP}$ and Pax7$^{CreER/+}$; Dcr$^{loxP/loxP}$; ROSA26eYFP/eYFP, respectively. To control for tamoxifen injection toxicity, we injected all mice with tamoxifen. Mice were housed and maintained in the Veterinary Medical Unit at Veterans Affairs Palo Alto Health Care Systems. Animal protocols were approved by the Administrative Panel on Laboratory Animal Care of Stanford University.

Satellite-Cell Isolation and FACS.

Hindlimb muscles were dissected and dissociated to yield a fragmented muscle suspension using gentle MACS dissociator (Miltenyi Biotec). The muscle suspension was then digested with Collagenase II (500 units per ml; Invitrogen) in Ham's F10 medium containing 10% horse serum (Invitrogen) for 90 min. Fragmented myofibers were washed and digested further in Collagenase II (100 units per ml) and Dispase (2 units per ml; Invitrogen) for 30 min. Digested-fiber suspensions were triturated and washed to yield a mononuclear cell suspension. Mononuclear cells were stained with Vcam-biotin (clone 429; BD Bioscience), CD31-APC (clone MEC 13.3; BD Bioscience), CD45-APC (clone 30-F11; BDBioscience) and Sca-1-Pacific-Blue (cloneD7; Biolegend) at 1:75. Streptavidin-PE-cy7 was used to amplify the Vcam signal (BD Biosciences, 1:75). Cell sorting was performed using a BD FACSAria II or BD FACSAria III cell sorter equipped with 488-nm, 633-nm and 405-nm lasers. The machine was carefully optimized for purity and viability, and sorted cells were subjected to FACS analysis directly after sorting to ensure purity. A small fraction of sorted cells was plated and stained for Pax7 and Myod to assess the purity of the sorted population.

Injections and Electroporation.

Mice were anaesthetized using isoflurane through a nose cone. Muscle injury was induced by injecting 1-2 µl of 1.2% BaCl$_2$ into approximately 25 sites in the lower hindlimb muscles. Electroporation of plasmid DNA into the tibialis anterior muscle was performed as described previously (Bertoni, C., et al. Proc. Natl Acad. Sci. USA 103, 419-424 (2006)) using a two-needle electrode array at a setting of 5 pulses of 50 ms duration at 150 V cm$^{-1}$. Antagomir molecules were injected into tail veins of 8-week-old mice at a dose of 8 mg kg$^{-1}$ body weight.

Antagomir synthesis. PAGE-purified RNAs were synthesized with modifications (Dharmacon). Sequences of single-stranded RNAs used in this study are as follows (*, phosphorothioate backbone at given position; ChI, cholesterol linked through a hydroxyprolinol linkage; m, 2'OMe-modified nucleotides): antagomir-489, 5'mG*mC*mUmGmCm-CmAmUmAmU mAmUmGmUmGmGmUmGmUm-C*mA*mU*mU*3'-ChI (SEQ ID NO:31); scramble, 5'mU*mU*mUmCmUmAmAmUmCmAmAmGmGm-UmCmUmGmUmG*mG*mC*mU*3'-ChI (SEQ ID NO:32).

Histology and Immunohistochemistry.

For haematoxylin and eosin staining, tibialis anterior muscles were dissected and directly frozen in OCT (Tissue-Tek). For immunohistology, tibialis anterior muscles were fixed for 5 h using 0.5% electron-microscopy-grade paraformaldehyde and subsequently transferred to 20% sucrose overnight. Muscles were then frozen in OCT, cryosectioned with a thickness of 6 µm and stained using an M.O.M kit (Vectorlabs) or a Zenon labeling kit (Invitrogen) according to the manufacturers' instructions.

miRNA and siRNA Transfections.

Approximately 40 fibers were placed in each well of a 6-well plate containing 1 ml of Ham's F10, 10% horse serum and 0.5% chicken embryo extract (US Biological). 100 nM of miR-489 or anti-miR-489 synthetic molecules (Ambion) were transfected into either freshly isolated single fiber explants or C2C12 cells using Lipofectamine 2000 (Invitrogen). Cells were collected for western blot 48 h after transfection. Control (cyclophilin B) and Dek siRNAs (Dharmacon) were dissolved and diluted as suggested by the manufacturer. Lipofectamine 2000 (Invitrogen) was used for the transfection of Dek siRNA according to the manufacturer's instructions.

Single-Fiber Explants.

EDL muscles were excised and digested in Collagenase II (500 units per ml in Ham's F10 medium) as previously described (Rosenblatt, J. D., Lunt, A. I., Parry, D. J. & Partridge, T. A., In vitro Cell Dev. Biol. Anim. 31, 773-779 (1995)). Fibers were then washed extensively and cultured in medium containing Ham's F10, 10% horse serum and 0.05% chick embryo extract. Every 24 h, 50% of the medium was replaced with Ham's F10 medium with 20% FBS. EDL fibers were cultured in suspension. Fixed fibers were stained and the number of satellite cells was quantified per fiber.

RT-PCR and miRNA Microarray.

Total RNA was isolated using Trizol (Invitrogen). For individual RT-PCR, Taqman probes were used for detecting miR-17, miR-27b, miR-206, miR-489, sno420, Gapdh, Ctr, Pax7 and myogenin mRNA expression (Applied Biosystems). For miRNA microarrays (Applied Biosystems), reverse transcription and amplification was performed as described by the manufacturer. Diluted cDNAs were loaded onto the Taqman Array Rodent MicroRNA A+B Cards Set v2.0 and qRT-PCR analysis was performed using an ABI 7900HT Fast Real-Time PCR System. miRNA gene expression was normalized to U6 small nuclear RNA. Relative quantitation of miRNA gene expression was performed using the delta delta CT method (Pfaffl, M. W., Nucleic Acids Res. 29, e45 (2001)). Data have been deposited at NCBI Gene Expression Omnibus under the accession number GSE26780.

DNA Cloning and Luciferase Assay.

A 300-base-pair genomic fragment flanking pre-miR-489 was cloned from mouse genomic DNA with the 5' primer CCCCATGAGGGCAGAAACCAT (SEQ ID NO:17) and the 3' primer TTATGATGCAACAAATATAT (SEQ ID NO:18). The fragment was then sub-cloned into pGEM-T-Easy (Promega) and inserted into pcDNA3.1 plasmid to generate CMV-miR-489 plasmid. To generate the miR-489 mutant plasmid, four point mutations were introduced into the miR-489 plasmid using the following primers: 489_m1-5' primer CTGCAGTGGCAGCTTGGTTTTCATATCT-GTAATGATACTTTCTAAAGTCTTCCAG (SEQ ID NO:19), 3' primer CTGGAAGACTTTAGAAAGTATCAT-TACAGATATGAAAACCAAGCTGCCACTGCAG (SEQ ID NO:20); 489_m2-5' primer CTTTCTAAAGTCTTCCA-GAATAACACTACAGATATG-GAAGCTAAACTGTTACATGGAACAAC (SEQ ID NO:21), 3' primer GTTGTTCCATGTAACAGTTTAGCT-TCCATATCTGTAGTGTTATTCTGGAA-GACTTTAGAAAG (SEQ ID NO:22).

These inserts (CMV-miR-489 and CMV-miR489-mutant) were then subcloned into pMR-Zsgreen1 to generate plasmids containing a ZsGreen reporter.

The Dek 3' UTR was cloned by amplifying the region of the Dek 3' UTR that contains miR-489-binding sites from mouse genomic DNA using the 5' primer AAGTGACAGATGT-TATT TTT (SEQ ID NO:23) and the 3' primer AACATTGATT-TATTCTTTAT (SEQ ID NO:24). The Dek UTR luciferase construct was generated by inserting this fragment into pMIR-report plasmid (Ambion). Dek mutants (m1, m2 and m3) were generated using the QuikChange II site directed mutagenesis kit (Stratagene).

For each putative miR-489 site, two point mutants were introduced to the seed sequence using the following primers: m1-5' primer GTTCTGCTTTGCCCTCAAAGTATAAT-CAATGTGGTTGTG (SEQ ID NO:25), 3' primer CACAAC-CACATTGATTATACTTTGAGGGCAAAGCAGAAC (SEQ ID NO:26), m2-5' primer GTCATCAATGTGGTTGT-GTTAACTCTAAGTATAATAGAAATTTTATAATGAGG (SEQ ID NO:27) (SEQ ID NO:27) 3' primer CCTCATTATAAAATTTCTAT-TATACTTAGAGTTAACACAACCACATTGATGAC (SEQ ID NO:28), m3-5' primer GTTGGCCTTTAAGCAATT-TATAATAAATCTTCACAATAAAGAATAAATC (SEQ ID NO:29), 3' primer GATTTATTCTTTATTGTGAAGATT-TATTATAAATTGCTTAAAGGCCAAC (SEQ ID NO:30).

Luciferase assays were performed by seeding $5 \times 10^5$ cells per well in 6-well plates. Cells were then transfected with 0.25 µg of 3' Dek UTR constructs, 0.75 µg of the miR-489 expression construct and 50 ng of the pRL-TK Renilla luciferase control vector. Cells were transfected using FuGENE 6 according to the manufacturer's instructions. Forty-eight hours after transfection, cells were lysed and luciferase activities were measured using the Dual Luciferase Assay System (Promega) with a 20/20n luminometer (Turner Biosystems).

The mouse pCMV-Sport6 Dek plasmid was purchased from Open Biosystems. The pCMV-Sport6 Dek deltaUTR construct was made by excising the Dek 3' UTR using restriction enzymes BgIII and Not I and re-ligated to generate a Dek expression plasmid without its 3' UTR.

Template-Strand Analysis.

Analysis of nonrandom template-strand segregation was performed as described with several modifications (Conboy, M. J., Karasov, A. O., & Rando, T. A., PLoS Biol. 5, e102 (2007)). Briefly, muscles of 8-week-old mice were injured as described and 200 µg of EdU (Invitrogen) were injected intraperitoneally 48 h and 52 h after injury. Satellite cells were then sorted using the scheme as described and plated on poly-L-lysine-treated chamber slides (BD Biosciences) coated with extracellular matrix gel (Sigma) diluted at 1:100 in DMEM medium. To facilitate the analysis of sister-cell pairs, sorted cells were plated at very low density (~10 cells per $mm^2$). After allowing cells to adhere for 1 h, cultures were treated with cytochalasinD (5 µM; Sigma) to prevent cytokinesis. Cells were fixed and stained using the Click-iT EdU Imaging Kit (Invitrogen) and antibodies recognizing Dek or Myod. Sister-cell pairs were identified as two nuclei less than one-cell-diameter apart with contiguous cytoplasm that was evident using brightfield microscopy. Between 200 and 250 cell pairs were scored per experiment and all experiments were performed in triplicate.

Western Blot Analysis.

Muscle tissues and cells were extracted in lysis buffer (50 mM Tris-HCl, pH 7.5, 0.5% SDS, 20 µg $ml^{-1}$ aprotinin, 20 µg $ml^{-1}$ leupeptin, 10 µg $ml^{-1}$ phenylmethylsulfonyl fluoride, 1 mM sodium orthovanadate, 10 mM sodium pyrophosphate, 10 mM sodium fluoride and 1 mM dithiothreitol). Protein extracts were subjected to electrophoresis on 4-15% polyacrylamide gradient gels and then transferred to nitrocellulose membranes. The membranes were incubated in blocking buffer (PBS and 5% milk) before overnight incubation with primary antibodies. After incubation with corresponding fluorescent secondary antibodies (Invitrogen), the membranes were analysed using the Odyssey imaging system (LI-COR). Glyceraldehyde-3-phosphate dehydrogenase or actin was used as a loading control.

Statistical Analysis.

All statistical analyses were performed using GraphPad Prism 5 (GraphPad Software). Unless otherwise noted, all error bars represent s.e.m.

Immunofluorescence and Antibodies.

Immunofluorescence was performed using a Zeiss Observer Z1 fluorescent microscope (Zeiss) equipped with a Hamamatsu Orca-ER camera or a Zeiss confocal system LSM710 (Zeiss). Data acquisition and fiber-diameter measurements were performed using Improvision Volocity software (Perkin Elmer) or Zeiss LSM ZEN software (Zeiss).

Antibodies.

The antibodies used in this study were Pax 7 (DSHB, 1:100), Ki67 (Abcam, 1:100 and BD Bioscience, 1:50), laminin (Sigma, 1:1,000), cleaved caspase3 (Cell signaling, 1:100), Myod (Dako, 1:1,000), green fluorescent protein (GFP) (Invitrogen, 1:250 and Abcam, 1:250), Dek (Proteintech Group, 1:2,000) and syndecan 4 (gift from Bradley Olwin, 1:1,000).

What is claimed is:

1. A method of altering muscle satellite cell quiescence, the method comprising:
   contacting a mammalian muscle satellite cell with a miR 489 inhibitory nucleic acid in a dose effective to down-regulate quiescence of the satellite cell, wherein the satellite cell is activated and proliferates.

2. The method of claim 1, wherein the nucleic acid is an siRNA or shRNA.

3. The method of claim 1, wherein the nucleic acid is an antisense oligonucleotide.

4. A method of altering muscle satellite cell quiescence, the method comprising:
   contacting by local administration a mammalian muscle-satellite cell with a miR 489 antisense oligonucleotide in a dose effective to down-regulate quiescence of the satellite cell, wherein the satellite cell is activated and proliferates, wherein the antisense oligonucleotide is a modified oligonucleotide that is complementary to miR-489, wherein the oligonucleotide is at least 12 but not more than 25 nucleotides in length and has no more than 2 mismatches over its length compared to an equal length portion of miR-489.

5. The method of claim 4 wherein said modified oligonucleotide comprises a cholesterol conjugate.

6. The method of claim wherein said modified oligonucleotide comprises one or more phosphorothioate linkages.

7. The method of claim 4 wherein said modified oligonucleotide comprises one or more sugar modifications.

8. The method of claim 4, wherein said muscle satellite cell is contacted in vitro.

9. The method of claim 4, wherein said muscle stem satellite cell is in vivo.

10. A method of altering muscle satellite cell quiescence, the method comprising:
   contacting by local administration a mammalian muscle satellite cell with a miR 489 antisense oligonucleotide in a dose effective to down-regulate quiescence of the satellite cell, wherein the satellite cell is activated and proliferates, wherein the antisense oligonucleotide is a modified oligonucleotide that is complementary to miR-489, wherein the oligonucleotide is at least 12 but not more than 25 nucleotides in length and has no more than 2 mismatches over its length compared to an equal length portion of miR-489; and
   monitoring proliferation or differentiation of the muscle satellite cells.

* * * * *

SEQUENCE LISTING

<160> NUMBER OF SEQ ID NOS: 32

<210> SEQ ID NO 1
<211> LENGTH: 22
<212> TYPE: RNA
<213> ORGANISM: Artificial Sequence
<220> FEATURE:
<223> OTHER INFORMATION: synthetic polynucleotide

<400> SEQUENCE: 1
ugcuugcccu caaaguguca uc                                            22

<210> SEQ ID NO 2
<211> LENGTH: 23
<212> TYPE: RNA
<213> ORGANISM: Artificial sequence
<220> FEATURE:
<223> OTHER INFORMATION: synthetic polynucleotide

<400> SEQUENCE: 2
cgacgguaua uacaccacag uaa                                           23

<210> SEQ ID NO 3
<211> LENGTH: 23
<212> TYPE: RNA
<213> ORGANISM: Artificial sequence
<220> FEATURE:
<223> OTHER INFORMATION: synthetic polynucleotide

<400> SEQUENCE: 3
uuguguuaac ucuaaguguc aua                                           23

<210> SEQ ID NO 4
<211> LENGTH: 23
<212> TYPE: RNA
<213> ORGANISM: Artificial sequence
<220> FEATURE:
<223> OTHER INFORMATION: synthetic polynucleotide

<400> SEQUENCE: 4
ggccuuuaag caauuuguca uaa                                           23

<210> SEQ ID NO 5
<211> LENGTH: 84
<212> TYPE: RNA
<213> ORGANISM: Homo sapiens

<400> SEQUENCE: 5
guggcagcuu ggggucgua ugugugacgc cauuuacuug aaccuuuagg agugacauca    60
cauauacggc agcuaaacug cuac                                          84

<210> SEQ ID NO 6
<211> LENGTH: 84
<212> TYPE: RNA
<213> ORGANISM: Macaca mulatta

<400> SEQUENCE: 6
guggcagcuu ggggucgua uguguggcgc cauuuacuug aaccuuuagg agugacauca    60
cauauacggc agcuaaacug uuac                                          84

<210> SEQ ID NO 7
<211> LENGTH: 84
<212> TYPE: RNA
<213> ORGANISM: Pongo pygmaeus

```
<400> SEQUENCE: 7
guggcagcuu gguggucgua ugugugggcgc cauuuacuug aaccuuuagg agugacauca    60
cauauacggc agcuaaacug cuac                                            84

<210> SEQ ID NO 8
<211> LENGTH: 83
<212> TYPE: RNA
<213> ORGANISM: Pan troglodytes

<400> SEQUENCE: 8
guggcagcuu ggugguucgua ugugugacgc cauuuacuug aaccuuuagg agugacauca    60
cauauacggc agcuaaacug cua                                             83

<210> SEQ ID NO 9
<211> LENGTH: 82
<212> TYPE: RNA
<213> ORGANISM: Bos Taurus

<400> SEQUENCE: 9
guggcagcuu ggugguucgua ugugugggcgc caucuacugg aacguuuagg agugacauca   60
cauauauggc gacuaaacug cu                                              82

<210> SEQ ID NO 10
<211> LENGTH: 84
<212> TYPE: RNA
<213> ORGANISM: Canis familiaris

<400> SEQUENCE: 10
guggcagcuu gguggccgua ugugugggcgc cauuuacuug aaccuuuagg agugacauca    60
cauauacggc ggcuaaacug cuac                                            84

<210> SEQ ID NO 11
<211> LENGTH: 107
<212> TYPE: RNA
<213> ORGANISM: Mus musculus

<400> SEQUENCE: 11
acugcugcag uggcagcuug guugucauau gugugaugac acuuucuaaa gucuuccaga     60
augacaccac auauuggca gcuaaacugu uacauggaac aacaagu                   107

<210> SEQ ID NO 12
<211> LENGTH: 106
<212> TYPE: RNA
<213> ORGANISM: Rattus norvegicus

<400> SEQUENCE: 12
acugcuacag uggcagcuug guugucguau gcgugaugac acguucucgu guauuccaga     60
augacaucac auauuggca gcuaaacugu uacaggaaca acaagu                   106

<210> SEQ ID NO 13
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 13
gugacaucac auauacggca gc                                              22
```

<210> SEQ ID NO 14
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 14
gugacaucac auauacggcg gc                                          22

<210> SEQ ID NO 15
<211> LENGTH: 23
<212> TYPE: RNA
<213> ORGANISM: Artificial sequence
<220> FEATURE:
<223> OTHER INFORMATION: synthetic polynucleotide

<400> SEQUENCE: 15
aaugacacca cauauauggc agc                                         23

<210> SEQ ID NO 16
<211> LENGTH: 24
<212> TYPE: RNA
<213> ORGANISM: Artificial sequence
<220> FEATURE:
<223> OTHER INFORMATION: synthetic polynucleotide

<400> SEQUENCE: 16
ugucguaugc gugaugacac guuc                                        24

<210> SEQ ID NO 17
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 17
ccccatgagg gcagaaacca t                                           21

<210> SEQ ID NO 18
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 18
ttatgatgca acaaatatat                                             20

<210> SEQ ID NO 19
<211> LENGTH: 55
<212> TYPE: DNA
<213> ORGANISM: Artificial sequence
<220> FEATURE:
<223> OTHER INFORMATION: synthetic polynucleotide

<400> SEQUENCE: 19
ctgcagtggc agcttggttt tcatatctgt aatgatactt tctaaagtct tccag      55

<210> SEQ ID NO 20
<211> LENGTH: 55
<212> TYPE: DNA
<213> ORGANISM: Artificial sequence
<220> FEATURE:
<223> OTHER INFORMATION: synthetic polynucleotide

<400> SEQUENCE: 20
ctggaagact ttagaaagta tcattacaga tatgaaaacc aagctgccac tgcag    55

<210> SEQ ID NO 21
<211> LENGTH: 62
<212> TYPE: DNA
<213> ORGANISM: Artificial sequence
<220> FEATURE:
<223> OTHER INFORMATION: synthetic polynucleotide

<400> SEQUENCE: 21
ctttctaaag tcttccagaa taacactaca gatatggaag ctaaactgtt acatggaaca    60
ac    62

<210> SEQ ID NO 22
<211> LENGTH: 62
<212> TYPE: DNA
<213> ORGANISM: Artificial sequence
<220> FEATURE:
<223> OTHER INFORMATION: synthetic polynucleotide

<400> SEQUENCE: 22
gttgttccat gtaacagttt agcttccata tctgtagtgt tattctggaa gactttagaa    60
ag    62

<210> SEQ ID NO 23
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 23
aagtgacaga tgttattttt    20

<210> SEQ ID NO 24
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 24
aacattgatt tattctttat    20

<210> SEQ ID NO 25
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 25
gttctgcttt gccctcaaag tataatcaat gtggttgtg    39

<210> SEQ ID NO 26
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 26

```
cacaaccaca ttgattatac tttgagggca aagcagaac                    39

<210> SEQ ID NO 27
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 27
gtcatcaatg tggttgtgtt aactctaagt ataatagaaa ttttataatg agg    53

<210> SEQ ID NO 28
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 28
cctcattata aaatttctat tatacttaga gttaacacaa ccacattgat gac    53

<210> SEQ ID NO 29
<211> LENGTH: 49
<212> TYPE: DNA
<213> ORGANISM: Artificial sequence
<220> FEATURE:
<223> OTHER INFORMATION: synthetic polynucleotide

<400> SEQUENCE: 29
gttggccttt aagcaattta taataaatct tcacaataaa gaataaatc         49

<210> SEQ ID NO 30
<211> LENGTH: 49
<212> TYPE: DNA
<213> ORGANISM: Artificial sequence
<220> FEATURE:
<223> OTHER INFORMATION: synthetic polynucleotide

<400> SEQUENCE: 30
gatttattct ttattgtgaa gatttattat aaattgctta aaggccaac          49

<210> SEQ ID NO 31
<211> LENGTH: 23
<212> TYPE: RNA
<213> ORGANISM: Artificial Sequence
<220> FEATURE:
<223> OTHER INFORMATION: synthetic polynucleotide

<400> SEQUENCE: 31
gcugccauau augugguguc auu                                      23

<210> SEQ ID NO 32
<211> LENGTH: 23
<212> TYPE: RNA
<213> ORGANISM: Artificial Sequence
<220> FEATURE:
<223> OTHER INFORMATION: synthetic polynucleotide

<400> SEQUENCE: 32
uuucuaauca agggucugug gcu                                      23
```